United States Patent [19]

Weitzberg et al.

[11] Patent Number: 5,079,260
[45] Date of Patent: Jan. 7, 1992

[54] METHOD FOR TREATING INFLAMMATION AND COMPOUNDS AND COMPOSITIONS SUITABLE FOR USE THEREIN

[75] Inventors: Moshe Weitzberg, Baltimore; Ronald Burch, Silver Spring; Barry Shearer, Baltimore, all of Md.

[73] Assignee: Nova Pharmaceutical Corporation, Baltimore, Md.

[21] Appl. No.: 529,356

[22] Filed: May 29, 1990

Related U.S. Application Data

[63] Continuation-in-part of Ser. No. 369,710, Jun. 22, 1989, abandoned.

[51] Int. Cl.$^5$ .............. A61K 31/235; C07C 229/00; C07C 269/00; C07C 233/00
[52] U.S. Cl. ................... 514/532; 560/155; 560/157; 560/170; 560/171; 564/155
[58] Field of Search ............... 514/532; 560/155, 157, 560/170, 171; 564/155

[56] References Cited

U.S. PATENT DOCUMENTS

| | | | |
|---|---|---|---|
| 2,877,269 | 3/1959 | van Campen et al. | 260/564 |
| 3,801,633 | 4/1974 | Toyoshima et al. | 260/518 |
| 3,835,175 | 9/1974 | Carpino et al. | 260/463 |
| 3,845,097 | 10/1974 | Toyoshima et al. | 260/471 |
| 3,906,031 | 9/1975 | Carpino et al. | 260/471 |
| 3,919,291 | 11/1975 | Toyoshima et al. | 260/482 |

OTHER PUBLICATIONS

Rosenthal et al., Immunopharmocologic Effects of Cycloleucine, J.P.E.T., 180(2): 501–513 (1972).
Ludwig et al., MER-27, a Suppressant of Non-Bacterial Pneumonia in Mice, Proc. Soc. Exp. Biol. Med. 100: 495–497 (1959).
Carpino, The 9-Fluorenylmethyloxycarbonyl Family of Base-Sensitive Amino-Protecting Groups, Acc. Chem. Res. 20: 401–407 (1987).

Primary Examiner—Stanley J. Friedman
Attorney, Agent, or Firm—Vincent L. Fabiano

[57] ABSTRACT

The present invention relates to a method of treating an inflammatory condition, and to compounds and composition suitable for use in such a method, which compounds have the Formula:

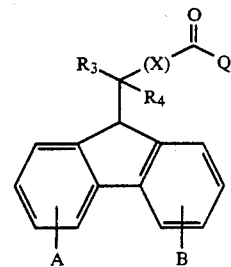

wherein:
X is methylene, ethylene, ethyleneoxy, or oxygen;
Q is

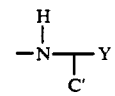

where C' is a residue of a lipophilic amino acid, and Y is —$CO_2H$, —$CH_2OH$, —$CONR_1R_2$, or —$CO_2R_1$ where $R_1$ and $R_2$ hydrogen, alkyl, or aryl;
$R_3$ and $R_4$ are, independently, hydrogen, alkyl or aryl; and
A and B are, independently, hydrogen, fused phenyl, alkyl, aryl, alkaryl, aralkyl, alkoxy, alkoxyalkyl, halogen, or nitro;
or pharmaceutically acceptable salts thereof.

57 Claims, No Drawings

METHOD FOR TREATING INFLAMMATION AND COMPOUNDS AND COMPOSITIONS SUITABLE FOR USE THEREIN

This application is a continuation-in-part of application Ser. No. 07/369,710, filed June 22, 1989.

BACKGROUND OF THE INVENTION

1. Technical Field

This invention relates to methods for treating inflammatory conditions and to compounds and pharmaceutical compositions suitable for therein.

2. Background Information

The treatment of inflammatory conditions, such as atopic dermatitis, contact dermatitis, psoriasis, rheumatoid arthritis, glomerulonephritis, osteoarthritis, lupus erythematosis, scleroderma, asthma and irritable bowel disease has, in the past, involved the use of agents such as aspirin-like nonsteroidal anti-inflammatory agents, glucocorticoids, methotrexate and cyclophosphamide. Unfortunately these agents generally produce unwanted side effects. Specifically, the nonsteroidal anti-inflammatory drugs often cause gastrointestinal and renal side effects. Glucocorticoids suppress the immune system, thus producing opportunistic infection and endocrinopathy. Methotrexate has been associated with patient death, and cyclophosphamide has carcinogenic liability. Thus, new agents for treating inflammatory conditions that are free of these adverse side effects are needed.

OBJECTS OF THE INVENTION

It is a general object of the present invention to provide a method of treating a subject suffering from an inflammatory condition while avoiding the adverse side effects associated with art-recognized anti-inflammatory agents. It is a further object of the invention to provide compounds and pharmaceutical compositions suitable for use in such a method.

Further objects and advantages of the invention will be clear to one skilled in the art from a reading of the description that follows.

SUMMARY OF THE INVENTION

The present invention relates to a method of treating a subject having an inflammatory condition, such as atopic or contact dermatitis, psoriasis, rheumatoid arthritis, glomerulonephritis, osteoarthritis, lupus erythematosis, scleroderoma, asthma or irritable bowel disease. The invention also relates to compounds and pharmaceutical compositions suitable for use in such a method.

In one embodiment, the present invention relates to a method of treating an inflammatory condition comprising administering to an animal in need of such treatment at least one compound of Formula I:

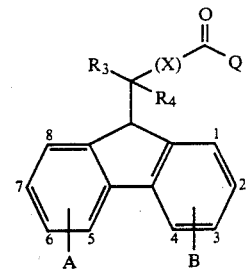

wherein:

X is methylene, ethylene, methyleneoxy, or oxygen;

Q is

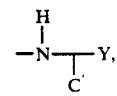

wherein C' is a residue of a lipophilic amino acid and Y is $-CO_2H$, $-CH_2OH$, $-CONR_1R_2$, or $-CO_2R_1$ where $R_1$ and $R_2$ are hydrogen, alkyl, or aryl;

$R_1$ and $R_4$ are, independently, hydrogen, alkyl or aryl; and

A and B are, independently, hydrogen, fused phenyl, alkyl, aryl, alkaryl, aralkyl, alkoxy, alkoxyalkyl, halogen, or nitro;

or a pharmaceutically acceptable salt thereof, in an amount sufficient to reduce or eliminate the inflammatory condition.

In a further embodiment, the present invention relates to a pharmaceutical composition comprising the compound of Formula I (above) in an amount sufficient to produce an anti-inflammatory effect, together with a pharmaceutically acceptable carrier.

In another embodiment, the present invention relates, generally, to compounds of Formula I wherein X, Q, $R_3$, $R_4$, A and B are defined as set forth above, providing that when $R_3$, $R_4$, A and B are hydrogen and Y is $-CO_2H$, (or salt thereof), X is not oxygen, and further providing that when A or B are, independently, hydrogen or halogen, $R_3$ and $R_4$ are hydrogen, X is oxygen, and Y is $-CO_2H$, (or salt thereof), C' is not an aromatic amino acid residue. The invention does, however, include N-[9H-(fluoren-9-ylmethoxy)carbonyl]-L-tert-leucine and N-[(9H-fluoren-9-ylmethoxy)carbonyl]-L-neopentylglycine.

DETAILED DESCRIPTION OF THE INVENTION

Compounds that are suitable for use in the method of treating an inflammatory condition of the present invention, are represented by the following Formula I:

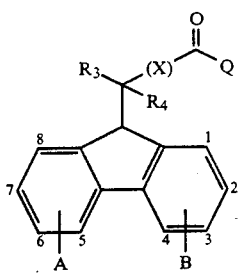

wherein:
X is methylene, ethylene, methyleneoxy, or oxygen;
Q is

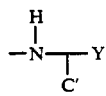

where C' is a residue of a lipophilic amino acid, and Y is —$CO_2H$, —$CH_2OH$, —$CONR_1R_2$, or —$CO_2R_1$ wherein $R_1$ and $R_2$ are hydrogen, alkyl (advantageously, $C_{1-8}$) or aryl (advantageously, $C_{6-12}$); and $R_3$ and $R_4$ are, independently, hydrogen, alkyl (advantageously, $C_{1-8}$) or aryl (advantageously, $C_{6-12}$); and A and B are, independently, hydrogen, fused phenol, alkyl (advantageously, $C_{1-9}$), aryl (advantageously, $C_{6-12}$), alkaryl (advantageously, ($C_{1-9}$)alk($C_{6-12}$)aryl), aralkyl (advantageously, ($C_{6-12}$)ar($C_{1-9}$)alkyl), alkoxy (advantageously, $C_{1-9}$), alkoxyalkyl (advantageously ($C_{1-9}$)alkoxy($C_{1-9}$)alkyl), halogen or nitro.

The above-named hydrocarbons can be unsubstituted or substituted with a $C_{1-4}$ alkyl group.

The term lipophilic amino acid as used herein includes within its scope amino acids, the residues of which do not contain free hydroxy groups, free thiol groups, or basic nitrogen atoms.

Pharmaceutically acceptable salts of the above-described compounds can be used in the compositions and methods to which the invention relates.

Certain of the compounds of Formula I described above are known in the art [see specifically compounds disclosed in U.S. Pat. Nos. 3,835,175 and 3,906,031 (see also U.S. Pat. No. 4,394,519)]. The remaining compounds are believed to be disclosed for the first time herein. The use of these agents (known and novel) in the treatment of inflammation has not been previously described.

Of the known compounds of Formula I, one that is preferred for use in the present method is the compound N-[(9H-fluoren-9-ylmethoxy)carbonyl]-L-leucine. In addition, N-[(9H-fluoren-9-ylmethoxy)carbonyl]-L-norleucine, and S-benzyl-$\beta,\beta$-dimethyl-N-[9H-(fluoren-9-ylmethoxy)carbonyl]-D-cystein, are also known compounds that are preferred for use in the present method.

The novel compounds of Formula I that are preferred for use in the present method are those wherein: i) $R_3$, $R_4$, A and B are hydrogen, X is methylene, and Q is a lipophilic amino acid; and ii) $R_3$ and $R_4$ are hydrogen, X is oxygen, A and/or B each represents at least one alkyl substituent, and Q is a lipophilic amino acid. The novel compounds of Formula I that are the most preferred for use in the present method are those wherein: i) $R_3$ and $R_4$ are hydrogen, X is oxygen, A is a methyl group located in the 4 position of the fluorene ring, B is hydrogen, and Q is the amino acid leucine; ii) $R_3$ and $R_4$ are hydrogen, X is oxygen, A is a methyl group located in the 4 position of the fluorene ring, B is hydrogen, and Q is the amino acid homophenylalanine; and iii) $R_3$ and $R_4$ are hydrogen, X is oxygen, A is a methyl group located in position 2 of the fluorene ring, B is a methyl group located in position 7 of the fluorene ring, and Q is the amino acid leucine.

The above compounds of Formula I can be prepared by methods known in the art (see also Examples below). For example, details of synthetic procedures suitable for use in preparing N-[9H-fluoren-9-ylmethoxy)carbonyl]-amino acids have been described by L. A. Carpino and G. Y. Han (U.S. Pat. Nos. 3,835,175 and 3,906,031) (see also Examples below). Typically, a 9H-fluorene is utilized as the starting material. This is converted to a corresponding 9H-fluoren-9-ylmethanol, for example, by condensation of a 9H-fluorene with methyl formate in the presence of sodium ethoxide, followed by reduction of the intermediate 9H-fluorene-9carboxaldehyde. Alternatively, 9H-fluorene can be condensed directly with formaldehyde in the presence of a strong base such as sodium hydride or sodium amide to give the 9-methanol derivative. Compounds in which the alpha carbon atom is substituted may be prepared by reaction between the selected 9H-fluorene and an aldehyde other than formaldehyde or a ketone, such as acetone or acetophenone, in the presence of a strong base.

Introduction of substituents in the benzo fused rings of the 9H-fluorene can be achieved by known procedures as, for example, by direct halogenation or nitration.

9H-Fluoren-9-ylmethanols are converted to 9H-fluoren-9-ylmethanol haloformates, carbonates, thiocarbonates, imidylcarbonates or other formate derivatives bearing a grouping ("leaving group") that is readily displaced by a nucleophilic nitrogen of an alpha amino acid. The resulting carbonyl derivatives of an activated 9H-fluoren-9-ylmethanol are condensed with an alpha aminocarboxylic acid to form a 9H-fluoren-9-ylmethoxycarbonyl derivative of the general Formula I. If the "leaving group" is halogen, especially chlorine, reaction may be effected in a polar organic solvent such as dioxane, tetrahydrofuran, dimethylformamide or pyridine under alkaline conditions (preferably mild) at a low temperature, for example from 0° C. to 25° C. during a period of from about 2 to 3 hours. A preferred solvent is a mixture of dioxane and water. Normally, the N-[(9H-fluoren-9-ylmethoxy)carbonyl]-amino acid precipitates from solution and may be purified, for example, by recrystallization. Utilization of other "leaving groups" may require somewhat elevated temperatures, for example, 25° C. to 50° C. and longer reaction times, for example, 8 to 12 hours.

The Examples below include further synthetic schemes for preparing the novel compounds to which the present invention relates.

The compounds of Formula I, where possible, are advantageously utilized as the free acid or in the form of a pharmaceutically acceptable salt with various inorganic or organic bases. Typical salts include the alkali metal or alkaline earth salts, although it will be appreciated that other nontoxic salts can also be used. Advantageously, compounds suitable for use in the present method this invention are administered as sodium, potassium, ammonium, choline or ethylenediamine salts. Sodium salts are preferred. As will be understood by those skilled in the art, the compounds of this invention can be present as D or L optical isomers or, in some cases, as diastereoisomers as well as racemates and diastereoisomeric mixtures. Unless otherwise specified, the compounds of Formula I include all isomers of such compounds, whether separated or mixtures thereof.

The activity of a compound of Formula I as an anti-inflammatory agent can be demonstrated in animals, such as mice, for example, by measuring the ability of the compound to inhibit edema caused by a variety of inflammatory agents that are generally accepted as producing irritation by differing mechanisms. Such inflammatory agents typically include tetradecanoylphorbolacetate, arachidonic acid, xylene, capsaicin, oxazolone, carrageenan and the like. The reverse passive Arthus test offers another measure of the compound's utility in preventing an inflammatory response (Chang et al, Eur. J. Pharm. 69:155-164 (1981)). Test compounds are typically administered intraperitoneally or topically. For intraperitoneal administration, the test compound can be given in dimethyl sulfoxide or in 0.5% methylcellulose 30 minutes prior to administration of the irritant. For topical administration, the test compound can be dissolved in, for example, acetone, ethanol or dimethyl sulfoxide and applied about 15 minutes prior to application of the irritant. Results can be expressed as the percent decrease in swelling in the compound-treated animals as compared to control animals that receive only the irritant.

It is noteworthy that currently available non-steroidal anti-inflammatory agents operate by a single mechanism (cyclo-oxygenase inhibitors), thus, they are highly active in a single assay (steroids are usually active in most, if not all, screens but have side effects that prohibit their widespread use). The compounds of Formula I are highly active in almost all of the inflammatory screens and are also highly active in the reverse passive artus assay and in adjuvant arthritis, which are considered to be predictive of activity against human arthritis. That is, the compounds of Formula I have the steroid-like spectrum of activity but lack steroid-like toxicity The pharmaceutical compositions of the present invention comprise, as an active ingredient, at least one compound acid of Formula I (see above), together with a pharmaceutically acceptable carrier. The active ingredient is present in the composition in an amount sufficient to produce an anti-inflammatory effect. The composition of the invention can be formulated so as to be suitable, for example, for oral, nasal, parenteral, topical, transdermal or rectal administration. (The compositions can also be formulated so as to be suitable for veternary use.)

Compounds (known and novel) that are preferred for use in the pharmaceutical composition of the present invention include those of Formula I wherein $R_3$ and $R_4$ are hydrogen, A and B are hydrogen or $(1-4)$ alkyl, X is oxygen, and Q is a lipophilic amino acid; compounds that are more preferred are those where A and B are alkyl; compounds that are the most preferred are those where A is a methyl group located in the 2 position of the fluorene ring and B is a methyl group located in the 7 position of the fluorene ring, and Q is leucine, isoleucine or nor-leucine.

Preferably, the pharmaceutical composition of the invention includes the active ingredient of Formula I in a quantity selected from 25 mg to 500 mg, advantageously, from about 50 mg to 250 mg, per dosage unit, depending on the route of administration. Appropriate concentrations and dosage unit sizes can be readily determined by one skilled in the art.

The pharmaceutical carriers used in the compositions of the invention may be, for example, in solid or liquid form. Exemplary of solid carriers are lactose, magnesium stearate, terra alba, sucrose, talc, stearic acid, gelatin, agar, pectin or acacia. The amount of solid carrier present in the composition will vary greatly but preferably will be from about 25 mg to 1 g. Exemplary of liquid carriers are syrup, peanut oil, olive oil, sesame oil, propylene glycol, polyethylene glycol (mol. wt. 200-400) and water. The carrier or diluent may include a time delay material well known to the art such as, for example, glyceryl monostearate or glyceryl distearate alone or with a wax.

As indicated above, the pharmaceutical composition of the invention can be present in dosage unit form. For example, the composition can take the form of a tablet (preferrably enteric coated), capsule (preferrably enteric coated), powder, troche, lozenge, inhalant, syrup, emulsion, gel, ointment, cream, lotion transdermal patch, suppository, sterile injectable liquid as well as a liquid suspension or solution. The pharmaceutical compositions of the present invention are prepared by conventional techniques such as by mixing, granulating and compressing or dissolving the ingredients as may be appropriate for the desired preparation.

The method of treating an inflammatory condition according to this invention comprises administering to a subject in need of such treatment an amount of at least one compound of Formula I (see above) sufficient to produce an anti-inflammatory effect. The compounds of Formula I can be administered orally, nasally, topically, transdermally, parenterally or anally, as may be required to effect the desired anti-inflammatory effect.

The active ingredient of Formula I (see above) will normally be administered in a daily dosage regimen selected from about 100 mg to 1 g, most preferably from about 200 mg to about 500 mg. Advantageously, equal doses will be administered, preferably, between one time per day to one time per week. The frequency of administration and the amount of active ingredient to be administered to effect treatment of a particular inflammatory condition can readily be determined by one skilled in the art. For inflammatory conditions of the lungs, an aerosol dispensing system wherein the active medicament is incorporated with Freon ® (fluorohydrocarbon) or other inert propellant in an aerosol container is of particular applicability. Such an aerosol system will deliver a metered dose of about 100 mcg to about 650 mcg, administered once or twice at a time as needed.

The following non-limiting Examples, which are illustrative of the compounds suitable for use in the methods and compositions of the present invention, demonstrate the activity of these compounds as well as processes for their preparation.

EXAMPLE 1

N-[(9H-Fluoren-9-ylmethoxy)carbonyl]-L-phenylalanine

9H-Fluoren-9-ylmethylchloroformate (51.4 g, 0.143 mole) and N-hydroxysuccinimide (29.0 g, 0.252 mole) were dissolved in 350 ml of dry, distilled dioxane. The mixture was cooled in ice and 27.9 ml of triethylamine was added slowly, so as to maintain the temperature of the mixture below 10° C. After four hours, the mixture was filtered to remove triethylammonium chloride. The solid was well washed with dioxane and the combined filtrates concentrated under reduced pressure. The product, 9-fluorenylmethyl-succinimidyl carbonate, 74 g, was crystallized by addition of petroleum ether and cooling to 4° C.

Phenylalanine (27.25 g, 0.165 mole) was dissolved in a solution of sodium carbonate (31.8 g, 0.3 mole) in 320 ml of water. This mixture was added to a solution of 9-fluorenylmethylsuccinimidyl carbonate (50.8 g, 0.15 mole) dissolved in a minimum amount of dioxane (approximately 90 ml being required). The mixture was stirred vigorously (mechanical stirring) at room temperature for 22 hours and then diluted with water. The reaction mixture was extracted twice with ethyl ether and then acidified to pH 2 with concentrated hydrochloric acid in the presence of 750 ml of ethyl acetate. The organic layer was separated, washed twice with 1 N hydrochloric acid, twice with water, once with brine, dried over anhydrous magnesium sulfate, and concentrated under reduced pressure. The product was crystallized by addition of hexane to the boiling ethyl acetate solution, to give 18 g of N-[(9H-fluoren-9ylmethyloxy)carbonyl]-L-phenylalanine, mp 179°–181° C.

EXAMPLE 2

N-[(9H-Fluoren-9-ylmethoxy)carbonyl]-L-leucine

To a solution of (1.31 g, 10 mmole) of L-leucine in 27 ml of water was added (2.5 g, 23 mmole) of sodium carbonate and the mixture was cooled in ice. To this was added a solution of (2.58 g, 7.2 mmole) of 9-fluorenylmethyl chloroformate in 20 ml of dioxane. The mixture was stirred at room temperature for 2.5 hours and diluted with 500 ml of water. The reaction mixture was extracted twice with ethyl ether. The aqueous layer was made acidic to Congo Red indicator paper with concentrated hydrochloric acid and the precipitate collected by filtration. The solid was recrystallized from ethyl acetate to give 0.9 g of N-[(9H-fluoren-9-ylmethyloxy)carbonyl)]-L-leucine, mp 151°–155° C.

EXAMPLE 3

Inhibition of Ear Edema Caused by Tetradecanoylphorbolacetate (I)

CF-1 Mice, 25-30 g body weight, six animals per group, were used. Test compounds (compounds of Formula I where X is oxygen, $R_3$, $R_4$, A and B are hydrogen and Q is as indicated in Table 1) were administered intraperitoneally (100 mg/kg) or topically as follows. For intraperitoneal administration, the test compound was dissolved in dimethyl sulfoxide or 0.5% methylcellulose and 100 μl was injected 30 minutes prior to irritant (100 mg/kg, i.p.). For topical administration, the test compound was dissolved in either acetone, ethanol or dimethyl sulfoxide and 5 μl (100 μg) applied to the upper surface (1 cm²) of the ear and an additional 5 μl (100 μg) applied to the lower surface (1 cm²) of the ear fifteen minutes prior to application of the irritant. A solution of the irritant, tetradecanoylphorbolacetate, 200 μg/ml, was added to the surface of the ear, 5 μl added to the upper surface and 5 μl to the lower surface. After three hours, the thickness of the ear was measured to 0.01 mm by a micrometer with loose drag positioned at the lateral-most edge of the mid-point of the pinna. Data were calculated as the inhibition by the test compound of increased ear thickness compared to control animals receiving only the irritant. The results are reported in Table 1.

TABLE 1

Inhibition of Ear Edema Caused by Tetradecanoylphorbolacetate

| Amino Acid | % Inhibition, intraperitoneal | % Inhibition, topical |
|---|---|---|
| L-Glycine | 38 | — |
| L-Alanine | 26 | — |
| L-Isoleucine | 48 | — |
| L-Valine | 46 | — |
| L-Homophenylalanine | 3 | — |
| L-Asparagine | 9 | — |
| L-Lysine | 14 | — |
| L-Tryptophan | 5 | — |
| D-Phenylalanine | 35 | — |
| L-Phenylalanine | 78 | — |
| D-Leucine | 54 | 21 |
| L-Leucine | 54 | 41 |
| L-Isoleucine | 48 | 39 |
| L-Methionine | 19 | — |
| Piroxicam (Feldene ®) (Reference Standard) | 40 | — |
| Dexamethasone (Reference Standard, 10 mg/kg) | 50 | — |

EXAMPLE 4

Inhibition of Ear Edema Caused by Arachidonic Acid (I)

CF-1 Mice, 25-30 g body weight, six animals per group, were used. Test compounds (compounds of Formula I where X is oxygen, $R_3$, $R_4$, A and B are hydrogen and Q is as indicated in Table 2) were administered intraperitoneally (100 mg/kg) as follows. For intraperitoneal administration, test compound was dissolved in DMSO or 0.5% methylcellulose and 100 μl was injected 30 minutes prior to i.p. administration of 100 mg/kg of arachidonic acid. A solution of the irritant, arachidonic acid, 100 mg/ml in ethanol, was added to the surface of the ear, 5 μl added to the upper surface and 5 μl to the lower surface. After sixty minutes, the thickness of the ear was measured to 0.01 mm by a micrometer with loose drag positioned at the lateral-most edge of the mid-point of the pinna. Data were calculated as the percent inhibition by the test compound of increased ear thickness compared to control animals receiving only the irritant. The results are reported in Table 2.

TABLE 2

Inhibition of Ear Edema Caused by Arachidonic Acid

| Amino Acid | % Inhibition, intraperitoneal | % Inhibition, topical |
|---|---|---|
| L-Glycine | 75 | — |
| L-Alanine | 62 | — |
| L-Isoleucine | 0 | — |
| L-Valine | 0 | — |
| L-Homophenylalanine | 24 | — |
| D-Phenylalanine | 70 | — |
| L-Phenylalanine | 70 | — |
| D-Leucine | 9 | 21 |
| L-Leucine | 62 | 41 |
| L-Isoleucine | 0 | 39 |
| Piroxicam (Feldene ®) | 86 | — |

EXAMPLE 5

Inhibition of Ear Edema Caused by Xylene (I)

CF-1 Mice, 25-30 g body weight, six animals per group, were used. Test compounds (compounds of Formula I where X is oxygen, $R_3$, $R_4$, A and B are hydrogen and Q is as indicated in Table 3) were administered intraperitoneally (100 mg/kg) or topically as follows. For intraperitoneal administration, the test compound was dissolved in DMSO or 0.5% methylcellulose and 100 μl was injected 30 minutes prior to irritant. For topical administration, test compound was dissolved in either acetone, ethanol or dimethyl sulfoxide and 5 μl (10 μg) applied to the upper surface (1 cm²) of the ear and an additional 5 μl (10 μg) applied to the lower surface (1 cm²) of the ear fifteen minutes prior to application of the irritant. The irritant, xylene, was added to the surface of the ear, 20 μl added to the upper surface and 20 μl to the lower surface. After two hours, the thickness of the ear was measured to 0.01 mm by a micrometer with loose drag positioned at the lateral-most edge of the mid-point of the pinna. Data were calculated as the inhibition by the test compound of increased ear thickness compared to that of control animals receiving only the irritant. The results are reported in Table 3.

TABLE 3

Inhibition of Ear Edema Caused by Xylene

| Amino Acid | % Inhibition, intraperitoneal | % Inhibition, topical |
|---|---|---|
| L-Glycine | 12 | 22 |
| L-Alanine | 39 | 27 |
| L-Valine | 27 | 19 |
| L-Homophenylalanine | 57 | 27 |
| D-Phenylalanine | 45 | — |
| L-Phenylalanine | 49 | 50 |
| D-Leucine | 35 | 0 |
| L-Leucine | 47 | 66 |
| L-Isoleucine | 40 | 39 |
| Piroxicam | 74 | — |
| $D\text{-}Pro^2\text{-}D\text{-}Trp^{7,9}$-Substance P (Reference Standard, 100 μg/ear) | 44 | |

EXAMPLE 6

Inhibition of Ear Edema Caused by Capsaicin

CF-1 Mice, 25-30 g body weight, six animals per group, were used. Test compounds (compounds of Formula I where X is oxygen, $R_3$, $R_4$, A and B are hydrogen and Q is as indicated in Table 4) were administered intraperitoneally (100 mg/kg) as follows. The test compound was dissolved in DMSO or 0.5% methylcellulose and 100 μl was injected 30 minutes prior to irritant. The irritant, capsaicin, 25 mg/ml, was added to the ear, 5 μl added to the upper surface and 5 μl to the lower surface. After thirty minutes, the thickness of the ear was measured to 0.01 mm by a micrometer with loose drag positioned at the lateral-most edge of the mid-point of the pinna. Data were calculated as the inhibition by the test compound of increased ear thickness compared to control animals receiving only the irritant. The results are reported in Table 4.

TABLE 4

Inhibition of Ear Edema Caused by Capsaicin

| Amino Acid | % Inhibition, intraperitoneal |
|---|---|
| L-Valine | 45 |
| L-Phenylalanine | — |
| D-Leucine | 66 |
| L-Leucine | 74 |
| L-Isoleucine | 44 |
| $D\text{-}Pro^2\text{-}D\text{-}Trp^{7,9}$-Substance P (Reference Standard, 100 μg/ear) | 34 |

EXAMPLE 7

Inhibition of Ear Edema Caused by Oxazolone (I)

CF-1 Mice, 25-30 g body weight, six animals per group, were used. The mice were sensitized to the irritant two weeks prior to the test by dribbling 100 μl of a 3% solution of oxazolone in acetone onto the abdominal skin of the animal. Test compounds (compounds of Formula I where X is oxygen, $R_3$, $R_4$, A and B are hydrogen and Q is as indicated in Table 5) were administered intraperitoneally as follows. The test compound was dissolved in DMSO or 0.5% methylcellulose and 100 μl (100 mg/kg) was injected 30 minutes prior to irritant. The irritant, 3% oxazolone in acetone, was added to the surface of the ear, 5 μl added to the upper surface and 5 μl to the lower surface. After twenty four hours, the thickness of the ear was measured to 0.01 mm by a micrometer with loose drag positioned at the lateral-most edge of the mid-point of the pinna. Data were calculated as the inhibition by the test compound of increased ear thickness compared to control animals receiving only the irritant. The results are reported in Table 5.

TABLE 5

Inhibition of Ear Edema Caused by Oxazolone

| Amino Acid | % Inhibition, intraperitoneal |
|---|---|
| L-Glycine | 45 |
| L-Alanine | 46 |
| L-Valine | 42 |
| L-Homophenylalanine | 58 |
| D-Phenylalanine | 52 |
| L-Phenylalanine | 62 |
| D-Leucine | 25 |
| L-Leucine | 58 |
| L-Isoleucine | 48 |
| Dexamethasone (at 10 mg/kg) Reference Standard | 48 |

EXAMPLE 8

Reverse Passive Artus Reaction (I)

Male CD rats weighing between 200 and 250 g were used. Test compounds (compounds of Formula I where X is oxygen, $R_3$, $R_4$, A and B are hydrogen and Q is as indicated in Table 6) were dissolved in dimethyl sulfoxide and 200 μl of this solution (100 mg/kg) were injected intraperitoneally one hour before administration of the antigen. The animals were anesthetized inhalationally with isoflurane and then were injected through the penile vein with 1 ml of a solution of 2.5 mg of Evan's blue dye and 5.0 mg of human serum albumin in 1 ml of saline. This treatment was followed immediately by intracutaneous injections of 0.03 ml of anti-human albumin diluted to contain 3.65 mg of antibody at 3 sites along the midline back. Anesthesia was terminated and after three hours the animals were sacrificed. The skin was removed and the blue stained areas cut out. The skin patches were soaked overnight in stoppered tubes containing 1 ml of 1 N potassium hydroxide at 37° C. Then 9 ml of a mixture of five parts of 0.6 N phosphoric acid and thirteen parts of acetone was added to the tubes. The tube contents were agitated and centrifuged, and the absorbance of the supernatant liquid was measured at 620 nm. The data were calculated as inhibition of blueing by test compound compared to control animals receiving only antigen and antibody. The results are reported in Table 6.

TABLE 6

Reverse Passive Artus Reaction

| Amino-Acid | % Inhibition, intraperitoneal |
|---|---|
| L-Glycine | 0 |
| L-Alanine | 18 |
| L-Valine | 30 |
| L-Homophenylalanine | 76 |
| L-Phenylalanine | 47 |
| D-Leucine | 42 |
| L-Leucine | 48 |
| L-Isoleucine | 31 |
| Colchicine (Reference Standard 1 mg/kg) | 64 |

EXAMPLE 9

N-[(9H-Fluoren-9-ylmethoxy)carbonyl]-N-methyl-L-leucine (NPC 15273)

A suspension of N-[(9H-fluoren-9-ylmethoxy)carbonyl]-L-leucine (1.67 g, 5 mmol) in toluene(100 ml) was charged with paraformaldehyde (1 g, 33.3 mmol) and 4-toluenesulfonic acid (100 mg, catalytic). The mixture was refluxed for 30 minutes in a Dean Stark apparatus for azeotropic distillation. The solution was washed with a saturated solution of sodium bicarbonate (×2), dried over magnesium sulfate and evaporated. The resulting oil in a 1:1 mixture of chloroform:trifluoroacetic acid (50 ml), at room temperature, was charged with triethylsilane (2.38 ml, 15 mmol). Stirring was continued for 22 hr. The solvents were removed in vacuum and the oil was crystallized from a mixture of ether:hexane. Recrystalyzation from EtOAc:hexane afforded 0.85 g (46%) of the product as a colorless solid, mp 101°-3° C.

EXAMPLE 10

N-{[9H-(4-Methylfluoren-9-yl)methoxy]carbonyl}-L-leucine (NPC 15325)

9-Hydroxyfluorene-4-methanol

A solution of 9-fluorenone-4-carboxylic acid (14.8 g, 66 mmol) in 250 mL of THF, at 0° C was charged with a solution of 1M borane-THF complex in THF (150 mL, 150 mmol). The temperature was slowly elevated to room temperature. After 1.5 hr at room temperature the reaction was quenched with water. The reaction mixture was diluted with EtOAc. The organic layer was washed with water (×3), dried over magnesium sulfate and evaporated. Recrystallization from ether with traces of EtOAc afforded 12.4 g (88.5%) of the diol.

4-Methylfluorene

A solution of 9-hydroxyfluoren-4-methanol (2.6 g, 12.2 mmol) in 1.1 EtOAc:AcOH was charged with catalytic amount of 10% palladium on charcoal. The mixture was treated with hydrogen under 1600 psi, at room temperature for three days. The catalyst was removed and the solvent was evaporated under reduced pressure. Recrystalyzation from MeOH afforded 1.7 g (77.0%) of the product as a light yellow solid.

4-Methyl-9-fluorenecarboxylic Acid

A solution of 4-methylfluorene (4.15 g, 23.0 mmol) in 120 mL THF at −78° C. was charged with a solution of 2.45 M BuLi in hexane (9.9 mL, 24.2 mmol). The color of the solution turned dark red and precipitation was apparent. After 45 minutes at −78° C. the reaction mixture was introduced with carbon dioxide gas (excess). The color soon disappeared and after 30 minutes at −78° C. the reaction mixture was warmed to room temperature. The reaction mixture was diluted with ether and ethyl acetate and the carboxylic salt was extracted with water twice. The combined aqueous phase was washed with ether then acidified with dilute HCl. The resulting solid was filtered, redissolved in ethyl acetate, dried with magnesium sulfate and evaporated. The resulting solid 3.15 g (61.1%) was carried on to the next step without further purification.

4-Methyl-9-fluorenemethanol

A solution of 4-methyl-9-fluorenecarboxylic acid (3.1 g, 13.8 mmol) in 90 mL of THF at 0° C., was charged with a solution of borane-THF (1M in THF, 27.6 mL, 27.6 mmol). The temperature was slowly elevated and the reaction mixture was stirred at room temperature overnight. The reaction was quenched with water, diluted with EtOAc, washed with water (×3), dried over magnesium sulfate and evaporated. The crude compound 2.8 g (96.5%) was pure enough to be carried as is to the next step. 4-Methylfluorenyl-9-methoxycarbonyl-L-leucine A solution of 4-methyl-9-fluorenemethanol (2.5 g, 11.9 mmol) in 20 mL of toluene, at 0° C. was charged with a solution of phosgene (20% in toluene, 12 g, 24 mmol). After 24 hours at room temperature additional excess of phosgene was introduced. After additional 2 hr at 50° C. and 2 hr at 90° C. in a sealed tube the reaction was stopped. The reaction was evaporated to dryness. The crude oil was dissolved in 20 mL dioxane then was added to a 40 mL suspension of L-leucine (3.12 g, 23.8 mmol) in 10% aqueous sodium carbonate. Additional dioxane was added in order to turn the slurry into an homogeneous solution. The reaction was completed within 15 minutes at room temperature. Part of the dioxane was evaporated in vacuum and the mixture was diluted with water. The aqueous phase was washed with ether (×3) then acidified with dilute HCl. The resulting product was purified on silica with 10% MeOH in chloroform. Further purification on a reverse phase silica (RP-18, from 1.1 to 4:6 MeOH:water) afforded 900 mg (20.6%) of the product as a colorless solid, mp 120°-2° C.

EXAMPLE 11

N-[(9H-Fluoren-9-ylmethoxy)carbonyl]-L-leucine methyl ester (NPC 15326)

A suspension of L-leucine methyl ester hydrochloride (3.0 g, 16.5 mmol) and sodium bicarbonate (large excess) in 30 mL of dioxane was charged with 9-fluorenemethoxycarbonyl-O-succinimide (2.5 g, 7.43 mmol) at room temperature. The reaction was monitored via TLC (silica, 25% EtOAc in hexane). After two hours 30 ml of methylene chloride was introduced and the reaction was stirred at room temperature for 48 hours. The solution was diluted with EtOAc, washed with water (×2), 3% aqueous HCl, water (×3) and brine. The solution was dried over magnesium sulfate and evaporated. The resulting oil was crystalized from hexane:ether to yield 1.9 g (62%) of colorless solid.

EXAMPLE 12

N-[(9H-Fluoren-9-ylmethoxy)carbonyl]-L-leucine ethyl ester (NPC 15327)

The reaction was carried out upon treating L-leucine ethyl ester hydrochloride with 9-fluorenemethoxycarbonyl-O-succinimide via the same procedure as described for Example 11: N-[(9H-fluoren-9-ylmethoxy)-carbonyl]-L-leucine methyl ester, and yielded 54.4%; mp 86°–7° C.

EXAMPLE 13

N-[(9H-Fluoren-9-ylmethoxy)carbonyl]-L-leucine benzyl ester (NPC 15328)

A solution Of L-leucine benzyl ester tosylate (5.8 g, 14.8 mmol) in 80 mL methylene chloride was stirred together with aqueous solution of saturated sodium bicarbonate (large excess) for 15 min at room temperature. The organic phase was separated, dried over magnesium sulfate and charged with 9-fluorenemethoxycarbonyl-O-succinimide (2.5 g, 7.4 mmol) at room temperature. The reaction was monitored via TLC (silica, 25% EtOAc in hexane). After two hours the reaction was over (according to its TLC with 25% EtOAc in hexane). However it was further stirred at room temperature for 48 hours. The solution was diluted with EtOAc then was washed with water (×2), 3% aqueous HCl, water (×3) and brine. The solution was dried over magnesium sulfate and evaporated. The resulting oil was crystallized from hexane:ether to yield 2.2 g (48.7%) of colorless solid, mp 91°–2° C.

EXAMPLE 14

2-{N-[(9H-Fluoren-9-ylmethoxy)carbonyl]amino}-4-methylpentanol (NPC 15427)

A solution of F-MOC-L-leucine (8 g, 22.6 mmol) in THF (22 ml), at 0° C., was charged with borane-THF complex (1M solution in THF, 45.3 mL, 45.3 mmol). After three hours of stirring at 0° C., the reaction mixture was quenched with 10% solution of AcOH in MeOH. The solvents were removed in vacuum and the residual oil was dissolved in EtOAc (100 mL). The organic solution was washed with 1N HCl, water (×2) and a saturated solution of sodium bicarbonate, dried over magnesium sulfate and evaporated. The residual oil was stirred for 48 hours in hexane. The precipitate was collected and recrystallized from EtOAc:hexane to yield 3.7 g (48.2%) of 2-[N-(9-fluorenylmethoxycarbonyl)amino]-4-methylpentanol as colorless solid, mp 131°–3° C.

EXAMPLE 15

N-[9H-Fluoren-9-ylmethoxy)carbonyl]-L-leucine 1-glyceryl ester (NPC 15430)

A solution of N-[9H-fluoren-9-ylmethoxy)carbonyl]-L-leucine (5 g, 14.1 mmol) and solketal (3.7 g, 28.3 mmol) in methylene chloride (50 mL) was charged with dicyclohexylcarbodiimide (3.65 g, 17.7 mmol). After 10 minutes the reaction was completed (upon monitoring with TLC on silica with 25% EtOAc in hexane). The solid was filtered off and the solvent was removed in vacuum. The crude product was then treated with HCl in acetone (70 mL) for 48 hr. The solvent was removed in vacuum and the crude product was dissolved in EtOAc. The organic solvent was washed with water (×3) dried over magnesium sulfate and evaporated. The resulting oil was purified on a column chromatography using from 50% to 70% EtOAc in hexane. Crystallization took place upon triturating the resulting oil in pentane to produce colorless solid 2.86 g (23.6%), mp 78°–83° C.

EXAMPLE 16

N-[3-(9H-Fluoren-9-yl)propionyl]-L-leucine (NPC 15476)

9-(2-Ethyl-1,3-dioxolane-2-yl)fluorene

A solution of BuLi (2.35 M in hexane, 25.6 mL, 60.2 mmol) was slowly added into a cooled (−78° C.) solution of fluorene (10 g, 60.2 mmol) in 200 mL THF. The reaction mixture turned dark red and solid started to precipitate out. After 30 minutes 2-(2-bromoethyl)-1,3-dioxolane (12 g, 66.3 mmol) was added to the cold solution and the solution was warmed up to room temperature. TLC (silica, 5% EtOAc in hexane) was used to monitor the reaction. After two hours the reaction was quenched with water and the product was extracted into EtOAc. The organic layer was washed with water (×3), dried over magnesium sulfate and evaporated. Short path chromatography afforded 8.34 g (52%) of the product as a colorless oil.

3-(Fluoren-9-yl)propionic Acid

A solution of 9-[2-(-2-ethyl-1,3-dioxolane)]-fluorene (8.3 g, mmol) in 350 mL acetone at 0° C. was slowly charged with 350 mL of Jone's reagent (the reagent was made by dissolving 16 g of chromium trioxide and 64 mL of concentrated sulfuric acid in 400 mL of water). A very strong reaction was observed during the addition of the oxidant. The temperature was raised to room temperature after all the reagent was added. The reaction mixture was monitored by TLC (silica, 25% EtOAc in hexane). The reaction was completed within 5 hr. The product was extracted with EtOAc and the organic layer was washed thoroughly with water (×6) until aqueous washings were clear and colorless. Recrystalyzation from MeOH:water afforded 6.5 g (87.5%).

N-[3-(9H-Fluoren-9-ylpropionyl)]-L-leucine t-butyl ester

A solution of 3-(fluoren-9-yl)propionic acid (3.0 g, 12.6 mmol) and leucine t-butyl ester (2.59 g, 13.8 mmol) in methylene chloride at room temperature (60 mL) was charged with 1-(3-dimethylaminopropyl)-3-ethylcarbodiimide hydrochloride (2.65 g, 13.8 mmol). After two hours at room temperature TLC (silica, 25% EtOAc in hexane) indicated the completion of the reaction. The methylene chloride was removed in vacuum and EtOAc was introduced. The organic solvent was washed with water (×2), 10% aqueous potassium carbonate and water again, dried over magnesium sulfate and evaporated. The resulting oil was filtered through a short column of silica with 25% EtOAc in hexane. The yield after evaporation was 4.25 g (82.8%).

N-[3-(9H-Fluoren-9-ylpropionyl)]-L-leucine

A solution of N-[3-(9H-fluoren-9-ylpropionyl)]-L-leucine t-butyl ester (4.2 g, 10.3 mmol) in 1:1 trifluoroacetic acid:methylene chloride was stirred overnight at room temperature. The solvents were removed in vacuum and the resulting oil was recrystallized from EtOAc: hexane to afforded 1 5 g (41.2%), mp 143°–5° C.

EXAMPLE 17

N-{[9H-(2-Methylfluoren-9-yl)methoxy]carbonyl}-L-leucine (NPC 15477)

2-Methylfluorene

A solution of 2-fluorenecarboxaldehyde (15 g, 77.1 mmol) in 250 mL of 10% solution of acetic acid in ethyl acetate was hydrogenated at 80 psi of hydrogen during 24 hours at room temperature over 20% palladium hydroxide on carbon (catalytic amount). The reaction was monitored by TLC (silica, 25% ethyl acetate in hexane). The catalyst was filtered off, evaporation of the solvents followed by recrystallization of the residual solid from ethanol:water 5:1 afforded 9.6 g (69.0%) of the product as colorless solid.

2-Methyl-9-fluorenecarboxylic Acid

A solution of 2-methylfluorene (6 g, 33.2 mmol) in 100 ml of THF at $-78°$ C. was charged with butyl lithium (2.18 g, 34.0 mmol). The reaction mixture was stirred for 15 min then $CO_2$ gaseous (5 g, 113.6 mmol) was introduced via a cannula over a period of 15 min at $-78°$ C. The reaction mixture was warmed up to room temperature and stirred for additional 2 hr until colorless. The reaction mixture was diluted with 250 mL of water and 100 mL of ethyl acetate, the layers were separated, the aqueous phase was washed with ethyl acetate ($3 \times 50$ mL) and acidified to pH 2 with conc. HCl. The precipitate was filtered off, washed with water and dried to afford 6.1 g (81.9%) of 2-methyl-9-fluorenecarboxylic acid.

2-Methyl-9-fluorenemethanol

A solution of 2-methyl-9-fluorenecarboxylic acid (6 g, 26.8 mmol) in 300 mL of THF at 0° C. was charged with IM THF solution of BH3-THF complex (53.5 mL, 53.5 mmol). The reaction mixture was stirred overnight then quenched with 30 mL of 10% acetic acid in methanol and diluted with 300 mL of water. The layers were separated, the aqueous phase was extracted with ethyl acetate ($3 \times 50$ mL), the combined extracts were dried over magnesium sulfate and evaporated to give colorless oil. Crystallization was accomplished upon treatment of the oil with 200 mL of hexane. Recrystallization from ethanol:water 4:1 afforded 4.55 g (80.6%) of 2-methyl-9-fluorenemethanol.

N-(2-Methylfluorenyl-9-methoxycarbonyl)-L-leucine

A solution of 2-methyl-9-fluorenemethanol (2 g, 9.5 mmol) in 15 mL of methylene chloride was charged with 4.2 M phosgene solution in methylene chloride (1.8 g,18.4 mmol) at room temperature. The reaction was monitored by TLC (silica, 25% ethyl acetate in hexane). The reaction mixture was stirred at room temperature for 6 days. Excess of phosgene was removed by bubbling argon. The solvent was evaporated to produce a slightly Yellow oil. The solution of the oil in 10 mL dioxane, at room temperature was charged with a solution of L-leucine (1.62 g, 12.3 mmol) in a mixture of 42 mL 10% aqueous potassium carbonate and 21 mL dioxane. The reaction mixture was stirred for 3 hr then diluted with water (20 mL). The aqueous layer was extracted with ethyl acetate ($5 \times 10$ mL) then acidified to pH 2 with HCl. The resulting oil was extracted with ethyl acetate ($4 \times 30$ mL). The organic extracts were combined, washed with 1N HCl ($2 \times 30$ mL) followed by washing with water, brine and evaporation of the solvent. The crude product was purified by column chromatography using RP-18 Silica, and 7:3 mixture of methanol:water as the eluent. This afforded 1.3 g (74.7%) of the desired compound as colorless solid, mp 125°–7° C.

EXAMPLE 18

N-[(2-Methoxyfluoren-9-ylmethoxy)carbonyl]-L-leucine (NPC 15489)

2-Methoxy-9-fluorenone

A solution of 2-hydroxyfluorenone (5 g, 25 5 mmol) in 500 mL methylene chloride was charged with 100 mL solution of 1N NaOH (4 g, 100 mmol), a solution of p-methyl tosylate (9.5 g, 51 mmol) in 200 mL of water and tetrabutylammonium hydrogen sulfate (0.2 g, catalytic) at room temperature. The reaction was monitored by TLC (silica, 25% ethyl acetate in hexane). The reaction mixture was stirred overnight at room temperature, the layers were separated. The organic layer was dried over MgSO. and evaporated. Short path chromatography of the residual solid (silica, 5% ethyl acetate in hexane) afforded 3.8 g (71.0%) of the methylated product.

2-Methoxy-9-fluorenol

A solution of 2-methoxy-9-fluorenon (6 g, 28.5 mmol) in 30 mL of THF was charged with 1M THF solution of $BH_3$-THF complex (60 mL, 60 mmol) at 0° C. The reaction mixture was stirred for 6 hr at room temperature, then quenched with water (100 mL). The resulting precipitate was filtered off, washed with water and dried to afford 5.6 g (93.3%) of pure 2-methoxy-9-fluorenol.

2-Methoxyfluorene

2-Methoxy-9-fluorenol (5.5 g, 25.9 mmol) was charged with acetic anhydride (50 mL). The reaction mixture was heated to 50°–60° C. for 3 hr then diluted with methanol (100 mL) and hydrogenated over 20% palladium hydroxide on carbon(catalytic) for 10 hr at 60–70 psi of hydrogen. The catalyst was filtered off and the solvents were removed under reduced pressure. Recrystallization from methanol-water afforded 2.6 g of the product. An additional portion was obtained (0.2 g) by dilution of the filtrate with a small amount of water. The total amount of the product was 2.8 g (55.2%).

2-Methoxy-9-fluorenecarboxylic Acid

A solution of 2-methoxyfluorene (2.7 g, 13.8 mmol) in 50 mL of THF at $-78°$ C. was charged with n-butyl lithium (0.93 g, 14.5 mmol). The reaction mixture was stirred for 15 min then CO, gaseous (5 g, 113.6 mmol) was introduced via cannula over a period of 15 min at $-78°$ C. The reaction mixture was warmed up to room temperature and stirred for additional 2 hr until a colorless solution was obtained. The reaction mixture was diluted with 100 mL of water and 100 mL of ethyl acetate. The layers were separated, the aqueous phase was washed with ethyl acetate ($5 \times 25$ mL) and acidified to pH 1 with concentrated hydrochloric acid. The precipitate was filtered off, washed with water and dried to afford 2.2 g (66.7%) of 2-methoxy-9-fluorenecarboxylic acid as colorless solid.

2-Methoxy-9-fluorenemethanol

A solution of 2-methoxy-9-fluorenecarboxylic acid (2.2 g, 9.2 mmol) in 100 mL of THF at 0° C. was charged with 1M THF solution of BH$_3$-THF complex (20 mL, 20 mmol). The reaction mixture was stirred overnight then quenched with 10 mL of 10% acetic acid in methanol an diluted with 100 mL of water. The layers were separated, the aqueous phase was extracted with ethyl acetate (3×25 mL). The combined extracts were dried over magnesium sulfate and evaporated. The residue was crystallized from methanol-water to afford 1.87 g (87.0%) of product.

N-{[9H-(4-Methylfluoren-9-yl)methoxy]carbonyl}-L-leucine

A solution of 2-methoxy-9-fluorenemethanol (1.2 g, 5.3 mmol) in 20 mL of anhydrous methylene chloride and 10 mL of anhydrous THF was charged with 4.2 M of phosgene solution in methylene chloride (2.38 mL, 10 mmol) at room temperature. The reaction was monitored by TLC (silica, 25% ethyl acetate in hexane). The reaction mixture was stirred at room temperature for 3 hr. The excess of phosgene was removed by argon bubbling. The solvent was evaporated to afford a slightly yellow oil. A solution of the oil in 5 mL of dioxane was charged with a solution of L-leucine (0.53 g, 4 mmol) in 14 mL of 10% aqueous solution of potassium carbonate and 7 mL of dioxane at room temperature. The reaction mixture was stirred overnight and diluted with water (100 mL). The water layer was extracted with ethyl acetate (5×30 mL) then acidified to pH 2 with HCl. The resulting oil was extracted with ethyl acetate (3×30 mL). The organic extracts were combined, washed with 1N HCl (2×30 mL) followed by washing with water, brine and evaporation of the solvent. The crude product was purified by recrystallization from ether-hexane mixture to afford 0.4 g (18.9%) of the desired product, mp 129°–131° C.

EXAMPLE 19

N-[9H-(2,3-Benzofluoren-9-ylmethoxy)carbonyl]-L-leucine (NPC 15510)

2,3-Benzofluorene-9-carboxylic Acid.

To a stirred, cooled (−78° C.) suspension of 6.73 g (31.1 mmol) of 2,3-benzofluorene in 75 mL of THF was added 13.2 mL (31.0 mmol) Of 2.35 M n-BuLi in hexanes dropwise. The resulting dark green mixture was stirred for 2 h and CO$_2$ gas generated from dry ice was passed into the reaction vessel for 1 h. The resulting pink mixture was warmed to room temperature, poured into water and washed twice with Et$_2$O. The combined organic layers were concentrated at reduced pressure, poured into water and washed with Et$_2$O. The combined aqueous layers were acidified with concentrated HCl and the precipitated solid was collected by vacuum filtration. Drying in vacuo afforded 5.69 g (71%) of the desired carboxylic acid, mp>225° C. (decomposition).

9-(2,3-Benzofluorenyl)methanol

To a stirred, cooled (0° C.) suspension of 5.66 g (21.7 mmol) of 2,3-benzofluorene-9-carboxylic acid in 25 mL of THF was added 22 mL (22.0 mmol) of 1.0 M BH$_3$ THF dropwise. The resulting yellow solution was allowed to warm to room temperature and stirred overnight. The mixture was quenched with 3 mL of 1:1 acetic acid-water and concentrated at reduced pressure. The resulting solid was dissolved in EtOAc and washed with saturated aqueous NaHCO$_3$. The aqueous layer was extracted with EtOAc and the combined organic layers were washed with brine and dried over magnesium sulfate. Solvent was removed at reduced pressure to afford 4.45 g (83%) of a yellow solid which was used without any further purification, mp 148°–152° C.

9-(2,3-Benzofluorenyl)methyl Chloroformate

To a stirred suspension of 4.40 g (17.8 mmol) of 9-(2,3-benzofluorenyl)methanol in 12 mL of methylene chloride was added 4.5 mL (18.9 mmol) of 4.2 M phosgene in methylene chloride. The mixture was allowed to stir for 48 h and solvent was removed at reduced pressure. The resulting reddish-brown solid was dried in vacuo to afford 5.01 g (91%) of the crude chloroformate which was used without any further purification.

N-[9H-(2,3-Benzofluoren-9-ylmethoxy)carbonyl]-L-leucine, tert-butyl ester

To a stirred solution of 3.20 g (17.1 mmol) of L-leucine tert-butyl ester in 10 mL of methylene chloride was added 1.83 g (17.2 mmol) of Na$_2$CO$_3$. The mixture was stirred for 10 min and 5.00 g (16.2 mmol) of crude 9-(2,3-benzofluorenyl)methyl chloroformate was added. A mild exothermic reaction occured and stirring was continued overnight. The mixture was poured into water and the aqueous layer was extracted with methylene chloride. The combined organic layers were washed with brine and dried over magnesium sulfate. Solvent was removed at reduced pressure and the crude product was chromatographed on 250 g of flash silica gel eluting with 15% EtOAc in hexane to afford 4.76 g (64%) of tert-butyl ester as a yellow solid, mp 51°–55° C.

N-[9H-(2,3-Benzofluoren-9-ylmethoxy)carbonyl]-L-leucine

To a stirred solution of 4.76 g (10.3 mmol) of N-[9H-(2,3-benzofluoren-9-ylmethoxy)carbonyl]-L-leucine, tert-butyl ester in 10 mL of methylene chloride was added 10 mL of trifluoroacetic acid. The mixture was stirred overnight and solvent was removed at reduced pressure. The crude product was chromatographed on 175 g of flash silica gel eluting with 25% EtOAc in hexane followed by 40% EtOAc in hexane to afford a dark yellow solid. Recrystallization from EtOAc-hexane afforded 2.35 g (56%) of analytically pure sample as a pale yellow solid, mp 168°–177° C.

EXAMPLE 20

N-[(9H-Fluoren-9-ylethoxy)carbonyl]-L-leucine (NPC 15521)

2-(9-Fluorenyl)ethanol

To a stirred, cooled (−78° C.) solution of 6.00 g (36.1 mmol) of fluorene in 75 mL of THF was added 15.4 mL (36.2 mmol) of 2.35 M n-BuLi in hexanes dropwise. The resulting dark orange mixture was stirred for 1.5 h and 26.0 mL (36.4 mmol) of 1.4 M ethylene oxide in Et$_2$O was added. The resulting bright orange mixture was warmed slowly to room temperature over 3.5 h, quenched with saturated aqueous NH$_4$Cl and concentrated at reduced pressure. The residue was poured into water and extracted twice with Et$_2$O. The combined organic layers were washed with brine and dried over magnesium sulfate. Solvent was removed at reduced pressure and the crude product was chromatographed on 150 g of flash silica gel eluting with 25% EtOAc in hexane to afford 5.05 g (67%) of the desired alcohol as a white solid, mp 98°–99° C.

2-(9-Fluorenyl)ethyl Chloroformate

To a stirred, cooled (0° C.) suspension of 4.50 g (21.4 mmol) of 2-(9-fluorenyl)ethanol in 10 mL of methylene chloride Was added 10.0 mL (42.0 mmol) of 4.2 M phosgene in methylene chloride. The resulting homogeneous yellow mixture was warmed to room temperature and stirred for 72 h. Solvent was removed at reduced pressure and the resulting dark green viscous oil was dried in vacuo to afford 5.74 g (98 %) of the crude chloroformate which was used without any further purification.

N-[(9H-Fluoren-9-ylethoxy)carbonyl]-L-leucine tert-butyl ester

To a stirred solution of 3.48 g (18.6 mmol) of L-leucine tert-butyl ester in 15 mL of methylene chloride was added 2.00 g (18.9 mmol) of $Na_2CO_3$. The suspension was stirred for 15 min and 5.00 g (18.3 mmol) of crude 2-(9-fluorenyl)ethyl chloroformate was added. A mild exothermic reaction occured and stirring was continued overnight. The mixture was poured into water and the aqueous layer was extracted with methylene chloride. The combined organic layers were washed with brine and dried over magnesium sulfate. Solvent was removed at reduced pressure and the crude product was chromatographed on 400 g of flash silica gel eluting with 10% EtOAc in hexane to afford 6.65 g (86%) of tert-butyl ester as a viscous pale yellow oil.

N-[(9H-Fluoren-9-ylethoxy)carbonyl]-L-leucine

To a stirred solution of 6.63 g (15.6 mmol) of N-[(9H-fluoren-9-ylethoxy)carbonyl]-L-leucine tert-butyl ester in 10 mL of methylene chloride was added 10 mL of trifluoroacetic acid. The mixture was stirred for 2.5 h and solvent was removed at reduced pressure. The crude product was chromatographed on 150 g of flash silica gel eluting with 25% EtOAc in hexane followed by 50% EtOAc in hexane to afford 5.32 g (92%) of product as a white solid, mp 42°-43° C.

EXAMPLE 2

N-[(9H-Fluoren-9-ylmethoxy)carbonyl]-L-leucine t-butyl ester (NPC 15527)

A solution of 9-fluorenemethoxycarbonyl-O-succinimide (9 g, 26.7 mmol) in methylene chloride (50 ml) was charged with leucine-t-butyl ester (5 g, 26.7 mmol). After 24 hours at room temperature the reaction mixture was thoroughly washed with water (×6), dried over magnesium sulfate and evaporated. Recrystalyzation from hexane (very small amount of EtOAc was added to increase solubility) afforded 6.5 g (59.5%) of the product as colorless solid, mp 183°-4° C.

EXAMPLE 22

N-[(9H-Fluoren-9-ylmethoxy)carbonyl]-L-leucine Amide (NPC 15528)

A solution of N-[(9H-fluoren-9-ylmethoxy)carbonyl]-L-leucine, acid chloride (3.5 g, 10 mmol) in 10 mL of THF was charged with $NH_3$ (29.6% water solution, 1.26 mL, 20 mmol) at room temperature. The reaction mixture was stirred for 30 min., then diluted with 100 mL of water and extracted with ethyl acetate (5×20 mL). The organic layers were combined, extracted with 10% potassium carbonate solution, washed with water, brine, dried and evaporated. Recrystallization of the product from ethanol afforded 1.26 g (36%) of N-(9-fluorenylmethoxycarbonyl)-L-leucine, amide as colorless solid, mp 79°-80° C.

EXAMPLE 23

N-[(9H-Fluoren-9-ylmethoxy)carbonyl]-L-leucine methylamide (NPC 15529)

A solution of N-[(9H-fluoren-9-ylmethoxy)carbonyl]-L-leucine, acid chloride (3.5 g, 10 mmol) in 50 mL of THF was charged with solution of methylamine (0.62 g, 20 mmol) in 50 mL of dichloromethane, at room temperature. The reaction mixture was stirred for 30 min. The solvents were removed and the residue was dissolved in 100 mL of ethyl acetate. The solution was washed with aqueous solution of 10% potassium carbonate, water, brine, dried over magnesium sulfate and evaporated. Recrystallization of the product from ethyl acetate/hexane mixture afforded 1.67g (46.6%) of N-[(9H-fluoren-9-ylmethoxy)carbonyl]-L-leucine methylamide, mp 173°-174° C.

EXAMPLE 24

N-[(9H-Fluoren-9-ylmethoxy)carbonyl]-L-tert-leucine, (NPC 15573)

A solution of L-tert-Leu (2 g, 15.3 mmol) in 100 mL of dichloromethane, at room temperature, was charged with F-MOC-O-succinimide (5.4 g, 16 mmol) and catalytic amount of DMAP. The reaction mixture was stirred for 48 hr. A solution of 10% aqueous potassium carbonate (50 mL) was added, and the mixture was stirred for additional 5 hr. The layers were separated, the water layer was diluted with 10% potassium carbonate solution (50 mL), extracted with ethyl acetate (3×30 mL) then acidified to pH 1. The oil was separated from the water layer, mixed with 1N HCl (30 mL) and extracted with ethyl acetate. The organic solution was washed with 1N HCl, water, brine and evaporated. Recrystallization of the product from ethyl acetate/hexane mixture afforded 2.3 g (40.6%) of F-MOC-L-tert-leucine as white solid, mp 122°-124° C.

EXAMPLE 25

N-{[9H-(1-Methylfluoren-9-yl)methoxy]carbonyl}-L-leucine (NPC 15638)

1-M Ⓡthyl-9-fluorenecarboxylic Acid

A solution of 1-methylfluorene (3.8 g, 21.1 mmol) in 100 mL of THF at −78° C. was charged with n-butyl lithium (3.5M solution in hexane, 6.29 ml, 22.0 mmol). The reaction mixture was stirred for 15 min, then $CO_2$ gaseous (5 g, 113.6 mmol) was introduced via cannula over a period of 15 min. The reaction mixture was warmed up to room temperature and stirring was continued until no color was apparent (approximately 2 hr). The slurry was diluted with water (100 mL) and ethyl acetate (50 mL). The layers were separated, the water layer was washed with ethyl acetate (3×50 mL), then acidified with conc. HCl. The precipitate was collected, washed with water and dried to give 1-methyl-9-fluorenecarboxylic acid (4.02 g, 84.8%).

1-Methyl-9-fluorenemethanol

A solution of 1-methyl-9-fluorenecarboxylic acid (4.0 g, 17.9 mmol) in 100 mL of THF was charged with 1M THF solution of $BH_3$-THF complex (35 mL, 35 mmol) at 0° C. The reaction mixture was stirred overnight at room temperature then quenched with water (20 mL). The organic layer was washed with 10% potassium carbonate solution, water, brine, dried and evaporated to afford 1-methyl-9-fluorenemethanol (3.2 g, 84.9%).

N-{[9H-(1-Methylfluoren-9-yl)methoxy]carbonyl}-L-leucine

A solution of 1-methyl-9-fluorenemethanol (3.0 g, 14.3 mmol) in a mixture of anhydrous THF and methylene chloride (1:1, 40 mL) was charged with a solution 4.2 M of phosgene in methylene chloride (5 mL, 21.0 mmol), at room temperature. The reaction mixture was stirred for 3 hr, then the excess of the phosgene was removed by bubbling argon. The solvents were removed, the residual oil was dissolved in 10 mL of dioxane and the solution was added to a solution of L-leucine (1.97 g, 15 mmol) in 22 mL of dioxane and 45 mL of 10% aqueous potassium carbonate at room temperature. The reaction mixture was stirred for two days, diluted with 150 mL of water and extracted with ethyl acetate (5×25 mL). The water layer was acidified to pH 1. The precipitated oil was extracted with ethyl acetate (3×50 mL), the organic solutions were washed with 1N HCl (3×20 mL), water, brine, dried over magnesium sulfate and evaporated to give an oil which was solidified by stirring in an ether-hexane mixture. The compound was purified by a column chromatography on silica using a solution of methanol: chloroform 95:5 as eluent. A second chromatography with RP-18 silica using methanol:water 7:3 afforded 1.3 g (24.7%) of the desired compound, mp 125°–128° C.

EXAMPLE 26

N-{[9H-(2,7-Dimethylfluoren-9-yl)methoxy]-carbonyl}-L-leucine (NPC 15669)

4,4'-Dimethyldiphenic Acid

Diazotation of the methyl anthranilic acid: a mixture of 2-amino-5-methylbenzoic acid (50.0 g, 330.8 mmol), water (136 mL) and conc. HCl (97.4 mL) was charged with a solution of sodium nitrite (23.8 g, 340.0 mmol) in 136 mL of water at 0°–5° C. during 30 min. The resulting diazonium solution was filtered and kept at a temperature below 5° C. before further use.

A solution of hydrated cupric sulfate (114.0 g, 457.6 mmol) in 454 mL of water was treated with concentrated ammonium hydroxide solution (sp.gr. 0.90, 190.4 mL). A solution of hydroxylammonium chloride (32.2 g, 464.0 mmol) in of water (108 mL) was charged with 6N sodium hydroxide (77 mL) at 5°–10° C.

The resulting hydroxylamine solution was immediately added to the cupric sulfate solution.

The resulting solution at 5°–10° C. was charged with the diazonium solution at the same temperature during 40–50 min (the rate of addition is about 10 cc per minute) with a vigorous stirring. Stirring was continued for 5 min then heated to 70° C. and acidified with conc. HCl. The mixture was allowed to stand overnight. The precipitate was filtered off, washed with water and dissolved in 400 mL of 10% sodium bicarbonate solution. This solution was treated with Norit, then filtered and acidified with 6N HCl. The precipitated product weighed 40.4 g (90.4%).

2,7-Dimethylfluorenone 4,4-Dimethyldiphenic acid (20.0 g, 74.0 mmol) was heated in a sand bath at 300°–330° C. for 2 hr until decarboxylation was over (no gas was evolved). The reaction mixture was cooled down to room temperature and the cake obtained was dissolved in acetone. Evaporation of the acetone produced a black material which was extracted with 25% solution of ethyl acetate in hexane. Evaporation of the solvents afforded the crude ketone which was further purified on a short path chromatography (silica, a. hexane, b. 5% ethyl acetate in hexane). This afforded 10.1 g (65.4%) of 2,7-dimethylfluorenone.

2,7-Dimethylfluorene

A mixture of 2,7-dimethylfluorenone (7.0 g, 32.8 mmol), methanol (100 mL), ethyl acetate (50 mL), acetic acid (20 mL) and palladium hydroxide (20% on carbon, water content 44.43%, 0.5g) was hydrogenated in a shaker at 26 psi of hydrogen for 4 hr. The reaction was monitored by TLC (silica, 10% ethyl acetate/hexane). The catalyst was filtered out and the solvents were removed in vacuum. Treatment of the residue with methanol afforded 5.7 g (89.3%) of 2,7-dimethylfluorene.

2,7-Dimethyl-9-fluorenecarboxylic Acid

A solution of 2,7-dimethylfluorene (5.0 g, 25.7 mmol) in THF (100 mL) at −78° C. was charged with butyl lithium (16.8 mL, 26.0 mmol). The reaction mixture was stirred for 15 min, then $CO_2$ gaseous (5g, 113.6 mmol) was introduced with cannula over a period of 15 min at −78° C. The reaction mixture Was Warmed up to room temperature and stirred overnight, diluted with water (150 mL). The layers were separated, the water layer was washed with ethyl acetate (5×20 mL), then acidified with conc. HCl. The precipitate formed was collected, washed with water and dried to give 4.4 g of 2,7-dimethyl-9-fluorenecarboxylic acid (72.4%).

2,7-Dimethyl-9-fluorenemethanol

A solution of 2,7-dimethyl-9-fluorenecarboxylic acid (4.3 g, 18.0 mmol) in THF (100 mL) was charged with 1M THF solution of $BH_3$-THF complex (36.0 mL, 36.0 mmol) at 0° C. The reaction mixture was stirred overnight at room temperature then quenched with water (100 mL) and HCl (3 mL). After addition of ethyl acetate (50 mL) the organic layer was separated and washed with 10% potassium carbonate solution, water, brine, dried over magnesium sulfate and evaporated to afford 2,7-dimethyl-9-fluorenemethanol (3.0 g, 74.4%).

N-{[9H-(2,7-Dimethylfluoren-9-yl)methoxy]carbonyl}-L-leucine

A solution of 2,7-dimethyl-9-fluorenemethanol (3.0 g, 13.4 mmol) in a mixture of anhydrous THF and methylene chloride (1:1, 50 mL) was charged with 4.2 M methylene chloride solution of phosgene (4.8 mL, 20.1 mmol) at room temperature. The reaction mixture was stirred overnight at room temperature, then an additional portion of phosgene (2.4 mL, 10.1 mmol) was added and the reaction mixture was stirred for additional 4 hr. The excess of the phosgene was removed by bubbling of argon. The solvents were removed under reduced pressure, the residue (a slightly pink crystals) was dissolved in 10 mL of dioxane and the solution was added to a solution of L-leucine (1.71 g, 13.0 mmol) in 25.0 mL of dioxane and 10% potassium carbonate solution (49.0 mL) at room temperature. The reaction mixture was stirred overnight, the dioxane was removed under reduced pressure, the residue was diluted with 150 mL of water. The water layer was extracted with ethyl acetate (5×25 mL), the combined organic extracts were washed 10% potassium carbonate solution, then twice with water. These water layers were combined with the original aqueous basic solution and the resulting solution was acidified to pH 1 with conc. HCl. The solid formed was filtered off and dried. The compound was purified by a column chromatography: silica RP-18, methanol:water 7.3. This afforded 2.74 g (57.3%) of the desired compound, mp 163°–166° C.

EXAMPLE 27

N-{[9H-(2,7-Dimethylfluoren-9-yl)methoxy]carbonyl}-L-leucine (NPC 15670)

6,6-Dimethyldiphenic Acid

Diazotation of the methyl anthranilic acid: a mixture of 2-amino-3-methylbenzoic acid (50.0 g, 330.8 mmol), water (136 mL) and conc. HCl (97.4 mL) was charged with a solution of sodium nitrite (23.8 g, 340.0 mmol) in 136 mL of water at 0°–5° C. during 30 min. The resulting diazonium solution was filtered and kept at a temperature below 5° C. before further use.

A solution of hydrated cupric sulfate (114.0 g, 457.6 mmol) in 454 mL of water was treated with concentrated ammonium hydroxide solution (sp.gr. 0.90, 190.4 mL). A solution of hydroxylammonium chloride (32.2 g, 464.0 mmol) in of water (108 mL) was charged with 6N sodium hydroxide (77 mL) at 5°–10° C. The resulting hydroxylamine solution was immediately added to the cupric sulfate solution.

The resulting solution was cooled to 5°–10° C. then was charged with the diazonium solution at the same temperature during 40–50 min (the rate of addition is about 10 cc per minute) with a vigorous stirring. Stirring was continued for 5 min then heated to 70° C. and acidified with conc. HCl. The mixture was allowed to stand overnight. The precipitate was filtered off, washed with water and dissolved in 400 mL of 10% sodium bicarbonate solution. This solution was treated with Norit, then filtered and acidified with 6N HCl. The precipitated product weighed 38.4 g (85.9%).

4,5-Dimethylfluorenone 4,4-Dimethyldiphenic acid (20.0 g, 74.0 mmol) was charged with polyphosphoric acid (83.4 g) at room temperature. The mixture was heated in an oil bath at 120°–121° C. for 6.5 hr until decarboxylation was over (no gas evolved). The reaction mixture was cooled down to 60° C., diluted with water (150 mL) then cooled down to room temperature. The precipitate was filtered off, washed with water, 10% sodium bicarbonate solution until the filtrate became colorless, extracted with 25% solution of ethyl acetate in hexane and dried over magnesium sulfate. Evaporation of the solvents gave the crude ketone which was purified by short path chromatography (5% ethyl acetate in hexane). This afforded 10.8 g (70.4%) of 4,5-dimethylfluorenone.

4,5-Dimethylfluorene

A mixture of 4,5-dimethylfluorenone (7.0 g, 32.8 mmol), methanol (100 mL), ethyl acetate (50 mL), acetic acid (20 mL) and palladium hydroxide (20% on carbon, water content 44.43%, 1.0 g) was hydrogenated in a shaker at 35–40psi of hydrogen for 3.5 hr. The reaction was monitored by TLC (silica, 10% ethyl acetate/hexane). The catalyst was filtered off and the solvent was removed in vacuum, the residue was diluted with water (150 mL). The product was extracted with ethyl acetate (3×50 mL) and dried over magnesium sulfate. Evaporation of the solvent afforded 5.8 g (91.2%) of 4,5-dimethylfluorene.

4,5-Dimethyl-9-fluorenecarboxylic Acid

A solution of 4,5-dimethylfluorene (5.2 g, 27.0 mmol) in 100 mL of THF at −78° C. was charged with butyl lithium (18.7 mL, 29.0 mmol). The reaction mixture was stirred for 15 min, then $CO_2$ gaseous (5 g, 113.6 mmol) was introduced via cannula over a period of 15 min at −78° C. The reaction mixture was warmed up to room temperature and stirred overnight. Water was added (150 mL) and the layers were separated, the water layer was washed with ethyl acetate (5×20 mL), then acidified with conc. HCl. The precipitate was collected, washed with water and dried to give 2,7-dimethyl-9-fluorenecarboxylic acid (4.24 g, 65.9 %).

4,5-Dimethyl-9-fluorenemethanol

A solution of 4,5-dimethyl-9-fluorenecarboxylic acid (4.2 g, 17.8 mmol) in 100 mL of THF was Charged with 1M THF solution of $BH_3$-THF complex (25.0 mL, 25.0 mmol) at 0° C. The reaction mixture was stirred overnight at room temperature then quenched with water (100 mL) and HCl (3 mL). After addition of ethyl acetate (50 mL) the organic layer was separated and washed with 10% potassium carbonate solution, water, brine, dried dried over magnesium sulfate and evaporated to afford 4.5-dimethyl-9-fluorenemethanol (3.0 g, 75.3%).

N-{[9H-(2,7-Dimethylfluoren-9-yl)methoxy]carbonyl}-L-leucine

A solution of 2,7-dimethyl-9-fluorenemethanol (3.0 g, 13.4 mmol) in a mixture of anhydrous THF and methylene chloride (1:1, 50 mL) was charged with a 4.2 M solution of phosgene (4.8 mL, 20.1 mmol) in methylene chloride at room temperature. The reaction mixture was stirred for 4 hr at room temperature. The excess of the phosgene was removed by bubbling argon. The solvents were removed under reduced pressure, the residue was dissolved in 10 mL of dioxane and the solution was added to a solution of L-leucine (1.71 g, 13.0 mmol) in 25.0 mL of dioxane and 49.0 mL of 10% potassium carbonate solution at room temperature. The reaction mixture was stirred overnight, the dioxane was removed under reduced pressure and the residue was diluted with 150 mL of water. The water layer was extracted with ethyl acetate (5×25 mL), the combined organic extracts were washed 10% aqueous solution of potassium carbonate, then twice with water. These water layers were combined with the original aqueous basic solution and the resulting solution was acidified to pH 1 with conc. HCl. The precipitate was filtered off and dried. The compound was purified by a column chromatography: silica RP-18, methanol:water 7:3. This afforded 1.94 g (38.1 %) of the desired compound as white solid, mp 135°–139° C.

EXAMPLE 28

N-{9H-[3-(2-Methylfluoren-9-yl)propionyl]}-L-leucine (NPC 15671)

3-(2-Methylfluoren-9-yl)-1,3-dioxolane

A solution of BuLi (2.35M in hexane, 20.5 mL, 47.9 mmol) was slowly added into a cooled (−78° C.) solution of 2-methylfluorene (8.2 g, 45.5 mmol) in 200 mL THF. The reaction mixture turned dark red and solid started to precipitate out. After 30 minutes 2(2-bromoethyl)-1,3-dioxolane (9.1 g, 50.3 mmol) was added to the cold solution and the solution was warmed up to room temperature. TLC (silica, 5% EtOAc in hexane) was used to monitor the reaction. After two hours, the reaction was quenched with water, the solution was concentrated and the product was extracted into EtOAc. The organic layer was washed with water ($\times 3$), dried over magnesium sulfate and evaporated. Short path chromatography (silica, 5% EtOAc in hexane) afforded 9.4 g.

3-(2-Methylfluoren-9-yl)propionic Acid

A solution of 3-(2-methylfluoren-9-yl)-1,3-dioxolane (9.0 g, 32 mmol) in 350ml acetone at 0° C. was slowly charged with 350 mL of Jone's reagent (the reagent was made by dissolving 16 g of chromium trioxide and 64 mL of concentrated sulfuric acid in 400 mL of water). A very strong reaction was observed during the addition of the oxidant. The temperature raised to room temperature after all the reagent was added. The reaction mixture was monitored by TLC (silica, 25% EtOAc in hexane). The reaction was completed within 5 hr. The product was extracted with EtOAc and the organic layer was washed thoroughly with water ($\times 6$), until aqueous washings were clear and colorless. Recrystallization from MeOH:water afforded 6.3 g.

N-{9H-[3-(2-Methylfluoren-9-yl)propionyl]}-L-leucine

A solution of 3-(2-methylfluoren-9-yl)propionic acid (3.4 g, 18 mmol) and leucine t-butyl ester (3.4 g, 18 mmol) in methylene chloride at room temperature (60 mL) was charged with 1-(3-dimethylaminopropyl)-3-ethylcarbodiimide hydrochloride (3.45 g, 18 mmol). Catalytic amount of DMAP (ca 50 mg) was added. After two hours at room temperature, TLC (silica, 25% EtOAc in hexane) indicated the completion of the reaction. The methylene chloride was removed in vacuum and EtOAc was introduced. The organic solvent was washed with water ($\times 2$), 10% aqueous potassium carbonate and water again, dried over magnesium sulfate and evaporated. The resulting oil was filtered through a short column of silica with 25% EtOAc in hexane. The crude oil was stirred overnight, at room temperature in in 1:1 trifluoroacetic acid: methylene chloride (60 mL). The solvents were removed in vacuum and the resulting oil was recrystallized from EtOAc: hexane to afforded 3.0 g (50.0%), mp 196°–200° C.

EXAMPLE 29

N-{[9H-(1-Methoxymethylfluoren-9-yl)methoxy]carbonyl}-L-leucine (NPC 15673)

1-Fluorenemethanol

A solution of 1-fluorenecarboxylic acid (10.0 g, 47.6 mmol) in THF (150 mL) at 0° C. was charged With a 1M solution of BH$_3$-THF complex in THF (80 mL, 80 mmol). The reaction mixture was stored overnight at room temperature then quenched with 30 mL of 10% AcOH in methanol. After dilution with water (100 mL), the water layer was extracted with ethyl acetate ($3 \times 50$ mL). The combined organic extracts were washed with 10% potassium carbonate solution, water, brine, dried over magnesium sulfate and evaporated. The residue (white crystals) was washed with ether and dried to afford 1-fluorenemethanol (6.4 g, 68.5%).

1-Methoxymethylfluorene

A solution of 1-fluorenemethanol (5.0 g, 25.6 mmol) in 50 mL of THF was charged with butyl lithium solution (11.0 mL, 26.0 mmol) at −78° C. After 15 min of stirring iodomethane (25.1 g, 176.1 mmol) was introduced. The reaction mixture was stirrer for 3 days at room temperature. The reaction was monitored by TLC (silica, 25% ethyl acetate in hexane). As soon as no more starting material was detected the reaction was quenched with water (30 mL). The organic layer was separated, washed with water, brine, dried over magnesium sulfate and evaporated. A short path chromatography of the residual oil (silica, 5% ethyl acetate in hexane) afforded 4.5 g (70.0%) of 1-methoxymethylfluorene.

1Methoxymethyl-9-fluorenecarboxylic Acid

A solution of 1-methoxymethylfluorene (4.5 g, 21.4 mmol) in 100 mL of THF at −78° C. was charged with butyl lithium (10.0 mL, 23.5 mmol). The reaction mixture was stirred for 15 min, then CO$_2$ gaseous (5g, 113.6 mmol) was introduced via cannula over a period 15 min at −78° C. The reaction mixture was warmed up to room temperature and stirred for additional 2 hr until colorless, diluted with water (100 mL) and ethyl acetate (50 mL). The layers were separated, the water layer was washed with ethyl acetate ($3 \times 50$ mL), then acidified with conc. HCl. The resulting precipitate was collected, washed with water and dried to give 1-methoxymethyl-9-fluorenecarboxylic acid (1.8 g, 33.1%).

1-Methoxymethyl-9-fluorenemethanol

A solution of 1-methoxymethyl-9-fluorenecarboxylic acid (3.4 g, 13.4 mmol) in 100 mL of THF was charged with 1M THF solution of BH$_3$-THF complex (30.0 mL, 30.0 mmol) at 0° C. The reaction mixture was stirred overnight at room temperature then quenched with water (100 mL). The organic layer was washed with 10% potassium carbonate solution, water, brine, dried over magnesium sulfate and evaporated. Short path chromatography of the residual oil (silica, 25% ethyl acetate in hexane) afforded 1-methoxymethyl-9-fluorenemethanol (2.6 g, 79.9%).

N-{[9H-(1-Methoxymethyllfluoren-9-yl)methoxy]carbonyl}-L-leucine, quarter hydrate A solution of 1-methoxymethyl-9-fluorenemethanol (2.6 g, 10.7 mmol) in a mixture of anhydrous THF and methylene chloride (1:1, 50 mL) was charged with 4.2 M solution of phosgene (3.8 mL, 16.1 mmol) in methylene chloride, at room temperature. The reaction mixture was stirred for 4 hr at room temperature. The excess of the phosgene was removed by bubbling argon. The solvents were removed, the residual oil was dissolved in 10 mL dioxane and the solution was added to a solution of L-leucine (1.31 g, 10.0 mmol) in 18.0 mL of dioxane and 37.5 mL of 10% potassium carbonate solution at room temperature. The reaction mixture was stirred overnight, diluted with 200 mL of water and extracted with ethyl acetate ($5 \times 20$ mL). The water layer was acidified to pH 1. The resulting oil was extracted with ethyl acetate ($3 \times 50$ mL), the organic solutions were washed with 1N HCl ($3 \times 20$ mL), water, brine, dried over magnesium sulfate and evaporated to give an oil which was purified by a column chromatography (silica RP-18, 60% methanol in water) to afford 1.6 g (37.4%) of the desired product, mp 63°–66° C.

EXAMPLE 30

N-[(9H-Fluoren-9-ylmethoxy)carbonyl]-L--neopentylglycine quarter hydrate (NPC 15676)

A solution of L-neopentylglycine (3.1 g, 21.5 mmol) in 10% aqueous potassium carbonate (40 ml) was added into a stirred solution of N-(9-fluorenylmethoxycarbonyl)succinimide (8.0 g, 23.7 mmol) in dioxane (100 ml). Catalytic amount of DMAP was added and the reaction mixture was stirred at room temperature for three hours. Most of the xylene was evaporated in vacuum. The resulting aqueous solution was washed with ether (×4). The aqueous solution was acidified with HCl and the precipitate was extracted with EtOAc. The organic phase was dried over magnesium sulfate and evaporated. Short path chromatography (silica, 2.5% EtOAc in hexane) afforded 3.5 g (43.7%), mp 70°–73° C.

EXAMPLE 31

N-[3-(9H-Fluoren-9-yl)propionyl]-L-tert-leucine, quarter hydrate (NPC 15685)

N-[3-(9H-Fluoren-9-yl)propionyl]-L-t-leucine quarter hydrate

A solution of 3-(fluoren-9-yl)propionic acid (2.4 g, 10 mmol) in thionyl chloride was refluxed for two hours. The reaction mixture was cooled down and the solvent was removed in vacuum. A solution of the resulting 3-(fluoren-9-yl)propionic acid chloride was dissolved in dioxane (20 mL) and added into a solution of L-tert-leucine (4 g, 30.5 mmol) in 10% aqueous sodium carbonate (40 mL). The reaction mixture was monitored by quenching an aliquot with methanol than monitor the resulting methyl ester by TLC (10% MeOH in chloroform). After an 1.5 hr water was added and most of the dioxane was removed in vacuum. The aqueous layer was washed with diethyl ether (×3) then was acidified to pH 1 with 10% HCl. The resulting precipitate was purified by a short path chromatography (silica, 5% MeOH in chloroform) to yield 1.5 g (42.1%), mp 79°–83° C.

EXAMPLE 32

N-{9H-[3-(1-Methylfluoren-9-yl)propionyl]}-L-tert-leucine, quarter hydrate (NPC 15885)

2-[2-(1-Methylfluoren-9-yl)ethyl]-1.3-dioxolane

1-Methylfluorene (3.2 g, 18.0 mmol) in 50 mL THF was charged with BuLi, 2.35M solution in hexanes (7.65 mL, 18.0 mmol) at −78° C. The reaction mixture was stirred for 2 hr at −78° C. then 2-bromo-1.3-dioxolane (3.6 g, 19.8 mmol) was added by a syringe. The reaction was monitored by TLC (silica, 10% ethyl acetate/hexane). The reaction mixture was stirred for 2 hr at room temperature then the THF was evaporated. The residue was dissolved in ethyl acetate. The solution was washed with water, dried over magnesium sulfate, treated with a coarse silica gel and Norit and evaporated to yield 4.8 g (96.6%) of the desired product.

3-(1-Methylfluoren-9-yl)propionic acid

2-[2-(1-Methylfluoren-9-yl)ethyl]-1,3-dioxolane (4.8 g, 17.2 mmol) in 100 mL of acetone was charged slowly with John's reagent (CrO₃: H₂SO₄:H₂O 4:4:50 by weight) at room temperature. The reaction was monitored by TLC (silica, 10% ethyl acetate/hexane). The reaction mixture was stirred for 6 hr at room temperature, the acetone was evaporated and the residual water was extracted with ethyl acetate twice. The combined organic layers were washed with water until water became colorless. The organic solution was then extracted with 1N aqueous solution of sodium hydroxide. The basic aqueous solution was washed with ethyl acetate, acidified and extracted with ethyl acetate again. The ethyl acetate solution was dried over magnesium sulfate and evaporated. Purification of the crude by short path chromatography (silica, 25% ethyl acetate/hexane) afforded 2.6 g (59.9%) of 3-(1-methylfluoren-9-yl)propionic acid.

3-(1-Methylfluoren-9-yl)propionyl Chloride 3-(1-Methylfluoren-9-yl)propionic acid (2.5 g, 9.9 mmol) was charged with SOCl₂ (20 mL, in excess) at room temperature. The reaction mixture was boiled for 2 hr. Excess of thionyl chloride was removed under reduced pressure. The residual oil was used for the next step without further purification.

N-{9H-[3-(1-Methylfluoren-9-yl)propionyl]}-L-tert-leucine, quarter hydrate

The compound 3-(1-methylfluoren-9-yl)propionyl chloride (2.7 g, 9.9 mmol) in 80 mL dioxane was charged with a solution of L-tert-leucine (1.6 g, 11.9 mmol) in 25 mL of 10% aqueous solution of potassium carbonate at room temperature. The reaction mixture was stirred overnight. The dioxane was removed under reduced pressure. The residue was diluted with water (100 mL), washed with ether (twice) then acidified to pH 1. The compound was extracted with ethyl acetate. Short path chromatography (Silica, 25% then 50% ethyl acetate/hexane) afforded 1.89 g (51.5%) of N-{9-[3-(1-methylfluoren-9-yl)propionyl]}-L-tert-leucine, quarter hydrate, mp 89°–94° C.

EXAMPLE 33

N-[3-(9H-Fluoren-9-yl)propionyl]-L-norleucine, quarter hydrate (NPC 15894)

3-(Fluoren-9-yl)propionyl Chloride 3-(Fluoren-9-yl)propionic acid (15.0 g, 62.9 mmol) was charged with SOCl, (20 mL, in excess) at room temperature. The reaction mixture was boiled for 2 hr. The reaction was monitored by TLC (silica RP-18, 70% methanol in water). Excess of thionyl chloride was removed under reduced pressure, the residue was crystallized from ethyl acetate/hexane mixture to give 10.1 g (62.5%) of the desired product. The product was not stable enough to be characterized and was used immediately for the next step.

N-[3-(9H-Fluoren-9-yl)propionyl]-L-norleucine, quarter hydrate

Crude 3-(fluoren-9-yl)propionyl chloride (without crystallization) (4.5 g, 17.5 mmol) in 20 mL of dioxane was added very slowly to a cooled (0° C.) solution of L-norleucine (2.7 g, 20.0 mmol) in 100 mL of 10% aqueous solution of sodium carbonate and 50 mL of dioxane. The reaction mixture was stirred for 1 hr at room temperature, diluted with water (50 mL) and extracted with ethyl acetate (2×25 mL). The water solution was cooled to 0° C. then acidified to pH 1 with 10% HCl. The semicrystalline residue was recrystallized from methanol/water. A pure sample was obtained after careful washing of the solid with ether. This afforded 1.7 g (27.4%) of N-[9H-(3-fluoren-9-ylpropionyl)]-L-norleucine, quarter hydrate, mp 167°-169° C.

EXAMPLE 34

N-[3-(9H-Fluoren-9-yl)propionyl]-L-Homophenylalanine, quarter hydrate (NPC 15895)

Crude 3-(fluoren-9-yl)propionyl chloride (described in Example 33, without crystallization) (3.8 g, 14.7 mmol) in dioxane (15 mL) was added very slowly to a cooled (0° C.) solution of L-homophenylalanine (2.7 g, 15.0 mmol) in 10% aqueous solution of sodium carbonate (90 mL) and 45 mL of dioxane. The reaction mixture was stirred for 1 hr at room temperature, diluted with water (100 mL) and extracted with ethyl acetate (3×25 mL). The water solution was cooled to 0° C. then acidified to pH 1 with 10% HCl. The precipitate was filtered off, washed with water, dried and carefully washed with ether (3×50 mL) to afford 1.7 g (28.6%) of N-[9H-(3-fluoren-9-ylpropionyl)]-L-homophenylalanine, quarter hydrate, mp 166°-168° C.

EXAMPLE 35

N-[3-(9H-Fluoren-9-yl)propionyl]-L-Phenylalanine (NPC 15896)

3-(Fluoren-9-yl)propionyl chloride (described in Example 33; without crystallization) (3.0 g, 11.7 mmol) in dioxane (40 mL) was added to a stirred solution of L-phenylalanine ((2.0 g, 11.7 mmol) in 75 mL of 10% potassium carbonate solution and 38 mL of dioxane at room temperature. The reaction mixture was stirred overnight. The dioxane was removed under reduced pressure. The residue was diluted with water (100 mL) and extracted with ethyl acetate (4×30 mL). The water solution was treated with Norit then acidified to pH 1. The precipitate was filtered off, washed with 1N HCl, water and dried. Short path chromatography (RP-18 Silica, 50% methanol/water) afforded white solid. Final purification was accomplished by washing the product with ether. The resulting yield of N-[9H-(3-fluoren-9-ylpropionyl)]-L-phenylalanine was 1.2 g 26.5%), mp 194°-195° C.

EXAMPLE 36

N-{[9H-(4-Methylfluoren-9-yl)methoxy]carbonyl}-L-tert-leucine (NPC 15904)

A solution of 4-methyl-9-fluorenemethanol (from Example 10, 4.5g, 21 5 mmol) in a mixture of anhydrous THF and methylene chloride (1:1, 50 mL) was charged with a solution of 4.2 M phosgene of 4.2 M phosgene methylene chloride (6 mL, 25.0 mmol) at room temperature. The reaction mixture was stirred for 24 hr at room temperature, then the excess of the phosgene was removed by bubbling argon. The solvents were removed in vacuum. The residual oil was treated with hexane (200 mL). The solids were removed by filtration and the solution was evaporated. The resulting oil was dissolved in dioxane (25 mL) then added to a solution of L-tert-leucine (2.9 g, 22.5 mmol) in a mixture of dioxane (34 mL) and 10% aqueous solution of potassium carbonate (68 mL) at room temperature. The reaction mixture was stirred overnight, diluted with water and extracted with ethyl acetate (5×30 mL). The water layer was acidified to pH 1. The precipitate was filtered, washed with water and dried. Short path chromatography (RP-18 Silica, 70% methanol/water) afforded an oil. The oil was dissolved in a solution of 10% aqueous potassium carbonate followed by precipitation with diluted HCl. Recrystallization from methanol/water (1.1) afforded 1.45 g (18.1%) of the desired compound, mp 91°-125° C.

EXAMPLE 37

N-{[9H-(1-Methylfluoren-9-yl)methoxy]carbonyl}-L-norleucine (NPC 15951)

A solution of 1-methyl-9-fluorenemethanol (its synthesis has been described in Example 25; 7.4 g, 35.2 mmol) in a mixture of anhydrous THF and methylene chloride (1:1, 90 mL) was charged with a solution of 4.2 M phosgene in methylene chloride (17 mL, 70.4 mmol) at room temperature. The reaction mixture was stirred for 24 hr at room temperature, then the excess of the phosgene was removed by bubbling argon. The solvents were removed in vacuum. The resulting yellow oil of the crude 1-methyl-9-fluorenylmethyl chloroformate was devided into three identical portions of 11.7 mmol each.

The resulting oil of ;-methyl-9-fluorenylmethyl chloroformate was dissolved in dioxane (50 mL) then added to a solution of L-norleucine (2.9 g, 23.6 mmol) in a mixture of dioxane (50 mL) and 10% aqueous solution of potassium carbonate (90 mL), at room temperature. The reaction mixture was stirred overnight, diluted with ethyl acetate (5×30 mL). The water layer was acidified to pH 1. The precipitate was filtered, washed with water and dried. Further purification on a short path chromatography (RP-18 Silica, from 50% to 70% methanol in water) afforded 2.1 g (16%) of the desired product, mp 130°-135° C.

EXAMPLE 38

N-{[9H-(1-Methylfluoren-9-yl)methoxy]carbonyl}-L-tert-leucine (NPC 15952)

A solution of 1-methyl-9-fluorenylmethyl chloroformate (prepared according to Example 37; 11.7 mmol) was dissolved in dioxane (50 mL) then added to a solution of L-norleucine (2.9 g, 23.6 mmol) in a mixture of dioxane (50 mL) and 10% aqueous solution of potassium carbonate (90 mL), at room temperature. The reaction mixture was stirred overnight, diluted with water and the organic impurities were extracted with ethyl acetate (5×30 mL). The water layer was acidified to pH 1. The precipitate was filtered, washed with water and dried. Further purification on a short path chromatography (RP-18 Silica, from 50% to 70% methanol in water) afforded 2.05 g (15.6%) of the desired product, mp 78°-81° C.

EXAMPLE 39

N-{[9H-(4-Methylfluoren-9-yl)methoxy]carbonyl}-L-homophenylalanine (NPC 15961)

A solution of 1-methyl-9-fluorenylmethyl chloroformate (prepared according to Example 37; 11.7 mmol) was dissolved in dioxane (50 mL) then added to a solution of L-homophenylalanine (4.23 g, 23.6 mmol) in a mixture of dioxane (50 mL) and 10% aqueous solution of potassium carbonate (90 mL), at room temperature. The reaction slurry was stirred overnight, diluted with water and acidified to pH 1. The resulting oil was purified on reverse phase Short path chromatography (RP-18 Silica, from 60% to 75% methanol in water) afforded 2.5 9 (17%) of the desired product, mp 104°-119° C.

EXAMPLE 40

N-{9H-[3-(2-Methoxyfluoren-9-yl)propionyl]}-L-leucine (NPC 15968)

2-[(2-Methoxyfluoren-9-yl)ethyl]-1,3-dioxolane

A solution of n-BuLi (2.5 M in hexane, 6.4 mL, 16.0 mmol) was slowly added into a cooled (−78° C.) solution of 2-methoxyfluorene (prepared according to example 10; 3.1 g, 15.8 mmol) in 100 ml THF. The reaction mixture became dark red and a solid started to precipitate out. After 30 minutes 2-(2-bromoethyl)-1,3-dioxolane (5.8 g, 32.0 mmol) was added to the cold solution and the solution was warmed up to room temperature. The reaction mixture was stirred overnight at room temperature. TLC (silica, 25% EtOAc in hexane) was used to monitor the reaction. The reaction was quenched with water and the product was extracted into EtOAc. The organic layer was washed with water (×3), dried over magnesium sulfate and evaporated. Short path chromatography (5% ethyl acetate/hexane) afforded 3.2 g (62.5%) of the product.

3-(2-Methoxyfluoren-9-yl)propionic Acid

A solution of 2-[(2-methoxyfluoren-9-yl)ethyl]-1,3-dioxolane (3.1 g, 10.0 mmol) in acetone (100 mL) at 0° C. was charged with Jone's reagent (90 mL) (the reagent was made by dissolving 16 g of CrO and 16 ml of $H_2SO_4$ (conc.) in 100 ml of water). The reaction mixture was stirred overnight at room temperature. The reaction was monitored by TLC (silica, 25% EtOAc in hexane). The acetone was evaporated, the residue was diluted with water (100 mL). The product was extracted into EtOAc and the organic layer was washed thoroughly with water (x6), until aqueous washings were clear, then the product was extracted into 1N NaOH solution (3×50 mL), the water was washed again with ethyl acetate (1×30 mL) and acidified to pH=1. The oil formed was extracted with ethyl acetate. The ethyl acetate solution was washed with water, brine, dried over magnesium sulfate and evaporated. The residue was dissolved in 25% ethyl acetate/hexane mixture and the solution was filtered through a layer of a coarse silica gel. Evaporation of the filtrate afforded 1.8 g (67.0%) of the 3-(2-methoxyfluoren-9-yl)propionic acid.

3-(2-Methoxyfluoren-9-yl)propionyl Chloride 3-(2-Methoxyfluoren-9-yl)propionic acid (1.6 g, 5.2 mmol) was charged with $SOCl_2$ (20 mL, in excess) at room temperature. The reaction mixture was boiled for 2 hr. The reaction was monitored by TLC (silica RP-18, 70% methanol/water). The excess of thionyl chloride was removed under reduced pressure, the residue (an oil) was used for the next step without further purification.

N-{9H-[3-(2-Methoxyfluoren-9-yl)propionyl]}-L-leucine

The compound above in 40 mL of dioxane was added to a stirred solution of L-leucine (1.3 g, 6.0 mmol) in 10% sodium carbonate solution (45 mL) and dioxane 21 mL) at room temperature. The reaction mixture was stirred overnight. The dioxane was removed under reduced pressure, the residue was diluted with water (100 mL), extracted with ethyl acetate (3×50 mL). The water solution was acidified to pH 1. The oil was extracted with ethyl acetate. The solution was washed with water, brine, dried and evaporated. Short path chromatography (RP Silica, 60–65% methanol/water) afforded 0.85 g (44.3%) of N-{9H-[3-(2-methoxyfluoren-9-yl)propionyl])-L-leucine, mp 135°–137°.

EXAMPLE 41

N-{9H-[3-(1-Methylfluoren-9-yl)propionyl]}-L-homophenylalanine (NPC-15974)

The compound 3-(1-methylfluoren-9-yl)propionyl chloride (its preparation was described in Example 32; 4.0 g, 14.8 mmol) in 80 mL dioxane was charged with a solution of L-homophenylalanine (3.5 g, 19.5 mmol) in 20 mL of 10% aqueous solution of sodium carbonate at room temperature. The reaction mixture was stirred for two hours. Most of the dioxane was removed under reduced pressure The residue was acidified, with HCl, to pH 1 and was extracted with ethyl acetate. The organic extract was concentrated and the crude product was purified via short path chromatography on reverse phase silica (RP-18 Silica, 25% then 70% methanol in water) to afforded 4.5 g (73%) of N-{9H-[3-(1-methylfluoren-9-yl)propionyl]}-L-homophenylalanine, mp 138°–140° C.

EXAMPLE 42

N-{9H-[3-(4-Methylfluoren-9-yl)propionyl]}-L-leucine quarter hydrate (NPC 15975)

2-[(4-Methylfluoren-9-yl)ethyl]-1,3-dioxolane

A solution of BuLi (2.5 M in hexane, 20.4 mL, 51.0 mmol) was slowly added into a cooled (−78° C.) solution of 4-methylfluorene (prepared according to Example 10; 9.0 g, 49.8 mmol) in 100 mL of THF. After 30 minutes 2-(2-bromoethyl)-1,3-dioxolane (18.9 g, 105.0 mmol) was added to the cold solution and the solution was warmed up to room temperature. The reaction mixture was stirred for weekend at room temperature. TLC (silica, 25% EtOAc in hexane) was used to monitor the reaction. The reaction was quenched with water and the product was extracted into EtOAc. The organic layer was washed with water (×3), dried over magnesium sulfate and evaporated. Short path chromatography (5% ethyl acetate/hexane) afforded 11.2 g (82.8%) of the product.

3-(4-Methylfluoren-9-yl)propionic Acid

A solution of 2-[(4-methylfluoren-9-yl)ethyl]-1,3-dioxolane (11.1 g, 39.6 mmol) in acetone (150 mL) at 0° C. was charged with Jone's reagent (16 g of $CrO_3$ and 16 ml of $H_2SO_4$ (conc.) in 100 ml of water). The reaction mixture was stirred overnight at room temperature. The reaction was monitored by TLC (silica, 25% EtOAc in hexane). The acetone was evaporated, the residue was diluted with water (100 mL). The product was extracted into EtOAc and the organic layer was washed thoroughly with water (×6), until aqueous washings were clear, then the product was extracted into 1N NaOH solution (3×70 mL), the water was washed again with ethyl acetate (1×30 mL) and acidified to pH=1. The solid formed was filtered off, washed with water and dried. This afforded 6.8 g (68.2%) of the 3-(4-methylfluoren-9-yl)propionic acid.

3-(4-Methylfluoren-9-yl)propionyl Chloride 3-(4-Methylfluoren-9-yl)propionic acid (3.5 g, 13 9 mmol) was charged with $SOCl_2$ (20 mL, in excess) at room temperature. The reaction mixture was boiled for 2 hr. The reaction was monitored by TLC (silica RP-18, 70% methanol/water). The excess of thionyl chloride was removed under reduced pressure, the residue (an oil) was used for the next step without further purification.

N-(9H-[3-(4-Methylfluoren-9-yl)propionyl]}-L-leucine, quarter hydrate

The compound above in 40 mL of dioxane was added to a stirred solution of L-leucine (2.6 g, 20.0 mmol) in 10% sodium carbonate solution (90 mL) and dioxane (45 mL) at room temperature. The reaction mixture was stirred overnight. The dioxane was removed under reduced pressure, the residue was diluted with water (100 mL), extracted with ethyl acetate (3×50 mL). The water solution was acidified to pH 1. The solid was filtered off, washed with water and dried. Short path chromatography (RP Silica, 60-65% methanol/water) afforded 1.8 g (36.0%) of N-{9H-[3-(4-methylfluoren-9-yl)propionyl]}-L-leucine, mp 125°-127° C.

EXAMPLE 43

N-[9H-[3-(1-Methylfluoren-9-yl)propionyl]}-L-norleucine, quarter hydrate (NPC 15976)

The compound 3-(1-methylfluoren-9-yl)propionyl chloride (its preparation was described in Example 32; 4.0 g, 14.8 mmol) in 80 mL dioxane was charged with a solution of L-norleucine (4.0 g, 30.5 mmol) in 20 mL of 10% aqueous solution of sodium carbonate at room temperature. The reaction mixture was stirred for two hours. Most of the dioxane was removed under reduced pressure. The residue was acidified, with HCl, to pH 1 and was extracted with ethyl acetate. The organic extract was concentrated and the crude product was purified via Short path chromatography on reverse phase silica (RP-18 Silica, 25% then 70% methanol in water) afforded 2.6 g (48%) of N-{9H-[3-(1-methylfluoren-9-yl)propionyl]}-L-norleucine, mp 128°-130° C.

EXAMPLE 44

Inhibition of Ear Edema Caused by Tetradecanoylphorbol Acetate (II)

CF-1 Mice, 25-30 g body weight, six animals per group were used. Test compounds were administered intraperitoneally or topically as follows. For intraperitoneal administration, the test compound was dissolved in dimethyl sulfoxide or 0.5% methylcellulose and 100 microliters was injected 30 minutes prior to irritant (100 mg/kg, i.p.). For topical administration, the test compound was dissolved in dimethyl sulfoxide, acetone, or ethanol and 5 microliters (100 micrograms) applied to the upper surface and an additional 5 microliters applied to the lower surface of the ear fifteen minutes prior to application of the irritant. A solution of the irritant, tetradecanoylphorbol acetate, 200 μg/mL, was added to the surface of the ear, 5 μL to the upper surface and 5 μL to the lower surface. After three hours, the thickness of the ear was measured to 0.01 mm by a micrometer with loose drag, positioned at the lateral-most edge of the mid-point of the pinna. Data were calculated as the inhibition of increased ear thickness compared to control animals receiving only the irritant. In general, % inhibition of equal to or greater than 20 % is statistically significant (p<0.05, or less, Student's t-test for unpaired data). The results are reported in Table 7.

TABLE 7

Inhibition of Ear Edema Caused By Tetradecanoylphorbol Acetate

| Compound | NPC Number | % Inhibition Intraperitoneal (dose, mg/kg) | % Inhibition Topical (dose, mg/kg) |
|---|---|---|---|
| Piroxicam (reference standard) | | 7 (10) 14 (30) 40 (100) | |
| Dexamethasone (reference standard) | | 50 (10) | |
| 4-Methylfluorenyl-9-methoxycarbonyl-L-leucine | 15325 | 36 (10) 11 (30) 82 (100) | |
| N-(9-Fluorenyl-methoxycarbonyl)-N-methyl-L-leucine, ethyl ester | 15327 | 37 (10) 64 (30) 77 (100) | |
| N-(9-Fluorenyl-methoxycarbonyl)-N-methyl-L-leucine, benzyl ester | 15328 | 49 (10) 47 (30) 62 (100) | |
| N-(9H-fluoren-9-ylpropionyl)-L-leucine | 15476 | 64 (100) | |
| N-(2-Methylfluorenyl-9-methoxycarbonyl)-L-leucine | 15477 | 35 (10) 37 (30) 72 (100) | |
| N-(2,3-Benzo-fluorenyl-9-methoxycarbonyl)-L-leucine | 15510 | 48 (10) 70 (30) 70 (100) | |
| N-(Fluorenyl-9-ethoxycarbonyl)-L-leucine | 15521 | 33 (10) 37 (30) 77 (100) | |
| N-[9H-(Fluoren-9-ylmethoxy)carbonyl]-L-leucine, tert-butyl ester | 15527 | 54 (10) 54 (30) 74 (100) | |
| N-[9H-(Fluorenyl-9-ylmethoxy)carbonyl]-L-leucine, amide | 15528 | 61 (10) 64 (30) 75 (100) | |
| N-[9H-(Fluorenyl-9-ylmethoxy)carbonyl]-L-leucine, methylamide | 15529 | 67 (10) 67 (30) 78 (100) | |
| N-[9H-(Fluorenyl-9-ylmethoxy)carbonyl]-L-tert-leucine | 15573 | 39 (10) 52 (30) 75 (100) | 20 (10) 31 (30) 38 (100) |
| N-[9H-(1-Methylfluorenyl-9-ylmethoxy)carbonyl]-L-leucine | 15638 | 23 (10) 12 (30) 62 (100) | |
| N-[9H-(Fluorenyl-9-ylmethoxy)carbonyl]-L-norleucine | 15667 | −80 (10) 72 (30) 180 (100) | |
| N-[9H-(2,7-Dimethylfluorenyl-9-methoxy)carbonyl-L-leucine | 15669 | 43 (10) 27 (30) 133 (100) | |
| N-[9H-(4,5-Dimethylfluorenyl-9-methoxy)carbonyl-L-leucine | 15670 | 27 (10) 117 (30) 150 (100) | |
| N-{9H-[3-(2-Methylfluorenyl-9]}-L-leucine-L-leucine | 15671 | 41 (10) 31 (30) 66 (100) | |
| N-{9H-[3-Fluorenyl-9)propionyl]}-L-leucine, sodium salt | 15672 | 54 (10) 21 (30) 66 (100) | |
| N-[9H-(1-Methoxymethylfluorenyl-9-methoxy)carbonyl]-L-leucine | 15673 | 0 (10) 33 (30) 60 (100) | |
| N-[9H-(Fluorenyl-9-ylmethoxy)carbonyl]-L-neopentylglycine | 15676 | 0 (10) 20 (30) 16 (100) | |
| N-(9H-Fluorenyl-9-ylpropionyl)-L-tert-leucine | 15685 | 0 (10) 16 (30) 67 (100) | |
| N-[9H-(1-Methyl-fluorenyl-9-ylpropionyl)]-L- | 15885 | 70 (10) 77 (30) 80 (100) | |

TABLE 7-continued

Inhibition of Ear Edema Caused By Tetradecanoylphorbol Acetate

| Compound | NPC Number | % Inhibition Intraperitoneal (dose, mg/kg) | % Inhibition Topical (dose, mg/kg) |
|---|---|---|---|
| leucine | | | |
| N-[9H-(3-Fluoren-9-ylpropionyl)]-L-norleucine | 15894 | 11 (10) 0 (30) 68 (100) | |
| N-[9H-(3-Fluoren-9-ylpropionyl)]-L-homophenylalanine | 15895 | 68 (10) 71 (30) 67 (100) | |
| N-[9H-(3-Fluoren-9-ylpropionyl)]-L-phenylalanine | 15896 | 0 (10) 0 (30) 84 (100) | |
| N-[9H-(4-Methyl-fluoren-9-ylmethoxy)carbonyl]-L-tert-leucine | 15904 | 16 (10) 0 (30) 43 (100) | |
| N-[9H-(1-Methyl-fluoren-9-ylmethoxy)carbonyl]-L-norleucine | 15951 | 41 (10) 39 (30) 70 (100) | |
| N-[9H-(1-Methyl-fluoren-9-ylmethoxy)carbonyl]-L-norleucine | 15952 | 27 (10) 75 (30) 67 (100) | |
| S-Benzyl-β,β-dimethyl-N-[9H-(fluoren-9-ylmethoxy)carbonyl]-D-cystein | 15953 | 64 (10) 87 (30) 95 (100) | |

EXAMPLE 45

Inhibition of Ear Edema Caused by Arachidonic Acid (II)

CF-1 mice, 25-30 g body weight, six animals per group, were used. The requisite amount of the test compound was dissolved is dimethyl sulfoxide or 0.5% methylcellulose and 100 μL of the solution was injected intraperitoneally 30 minutes prior to the administration of 100 mg/kg of arachidponic acid. A solution of this irritant, b 100 mg/mL in ethanol, was applied to the surface of the ear, 5 μL to the upper surface and 5 μL to the lower surface. After sixty minutes, the thickness of the ear was measured to 0.01 mm by a micrometer with the loose drag positioned at the lateral-most edge of the mid-point of the pinna. Data were calculated as the percent inhibityion by the test compound of increased ear thickness compared to control animals recieveing only the irritant. In general, % inhibition of equal to or greater than 20% is statistically significant (p, 0.05, or less, Student's t-test for unpaired data). The results are reported in Table 8.

TABLE 8

Inhibition of Ear Edema Caused by Arachidonic Acid

| Compound | NPC Number | % Inhibition Intraperitoneal (dose, mg/kg) |
|---|---|---|
| Piroxicam (reference standard) | | 56 (10) 77 (30) 86 (100) |
| Dexamethasone (reference standard) | | 12 (10) |
| Indomethacin (reference standard) | | 1 (100) |
| 4-Methylfluorenyl-9-methoxycarbonyl-L-leucine | 15325 | 52 (10) 63 (30) 100 (100) |
| N-(2-Methylfluorenyl-9-methoxycarbonyl)-L-leucine | 15477 | 10 (10) 58 (30) 82 (100) |
| N-(2,3-Benzofluorenyl-9-methoxycarbonyl-L-leucine | 15510 | −24 (10) 69 (30) 67 (100) |
| N-(Fluorenyl-9-ethoxycarbonyl)-L-leucine | 15521 | 34 (10) 41 (30) 69 (100) |
| N-[9H-(Fluoren-9-ylmethoxy)carbonyl]-L-leucine, tert-butyl ester | 15527 | 21 (10) 47 (30) 68 (110) |
| N-[9H-(Fluorenyl-9-ylmethoxy)carbonyl]-l-leucine, amide | 15528 | 31 (10) 32 (30) 35 (100) |
| N-[9H-(Fluorenyl-9-ylmethoxy)carbonyl]-L-leucine, methylamide | 15529 | 16 (10) 32 (30) 29 (100) |
| N-[9H-(Fluorenyl-9-ylmethoxy)carbonyl]-L-tert-leucine | 15573 | 27 (10) 32 (30) 42 (100) |
| N-[9H-(1-Methylfluorenyl-9-ylmethoxy)carbonyl]-L-leucine | 15638 | 65 (100) |
| N-[9H-(Fluorenyl-9-ylmethoxy)carbonyl]-L-norleucine | 15667 | 7 (10) 57 (30) 65 (100) |
| N-[9H-(2,7-Dimethylfluorenyl-9-methoxy)carbonyl-L-leucine | 15669 | 12 (10) 22 (30) 60 (100) |
| N-{9H-[3-(2-Methylfluorenyl-9]}-L-leucine-L-leucine | 15671 | 40 (10) 19 (30) 56 (100) |
| N-[9H-(1-Methoxymethylfluorenyl-9-methoxy)carbonyl]-L-leucine | 15673 | 24 (10) 27 (30) 58 (100) |
| N-[9H-(Fluorenyl-9-ylmethoxy)carbonyl]-L-neopentylglycine | 15676 | 20 (10) 44 (30) 79 (100) |
| N-(9H-Fluorenyl-9-ylpropionyl)-L-tert-leucine | 15685 | 44 (10) 61 (30) 69 (100) |
| N-[9H-(1-Methylfluorenyl-9-ylpropionyl)]-L-leucine | 15885 | 52 (10) 71 (30) 79 (100) |
| N-[9H-(3-Fluoren-9-ylpropionyl)]-L-norleucine | 15894 | 22 (10) 40 (30) 60 (100) |
| N-[9H-(3-Fluoren-9-ylpropionyl)]-L-homophenylalanine | 15895 | 14 (10) 26 (30) 52 (100) |
| N-[9H-(3-Fluoren-9-ylpropionyl)]-L-phenylalanine | 15896 | 16 (10) 24 (30) 72 (100) |
| N-[9H-(4-Methylfluoren-9-ylmethoxy)carbonyl]-L-tert-leucine | 15904 | 19 (10) 54 (30) 79 (100) |
| N-[9H-(1-Methylfluoren-9-ylmethoxy)carbonyl]-L-norleucine | 15951 | 11 (10) 18 (30) 56 (100) |
| N-[9H-(1-Methylfluoren-9-ylmethoxy)carbonyl]-L-norleucine | 15952 | 43 (10) 47 (30) 50 (100) |
| S-Benzyl-β,β-dimethyl-N-[9H-(fluoren-9-ylmethoxy)carbonyl]-D-cystein | 15953 | 46 (10) 66 (30) 60 (100) |

Inhibition of Ear Edema Caused by Xylene (II)

CF-1 mice, 25-30 g body weight, six animals per group, were used. The requisite amount of the test compound was dissolved is dimethyl sulfoxide or 0.5% methylcellulose and 100 μL of the solution was injected intraperitoneally 30 minutes prior to the administration the irritant. The irritant xylene was applied to the surface of the ear, 20 μL to the upper surface and 20 μL to the lower surface, After two hours, the thickness of the ear was measured to 0.01 mm by a micrometer with the loose drag positioned at the lateral-most edge of the mid-point of the pinna. Data were calculated as the percent inhibition by the test compound of increased ear thickness compared to control animals receiving only the irritant. In general, % inhibition of equal to or greater than 20% is statistically significant (<0.05, or less, Student's t-test for unpaired data). The results are reported in Table 9.

TABLE 9

Inhibition of Ear Edema Caused by Xylene

| Compound | NPC Number | % Inhibition (dose, mg/kg) |
|---|---|---|
| Piroxicam (reference standard) | | 53(10) 49(30) 74(100) |
| Dexamethasone (reference standard) | | 34(10) |
| 4-Methylfluorenyl-9-methoxycarbonyl-L-leucine | 15325 | 16(10) 25(30) 78(100) |
| N-(9-Fluorenylmethoxycarbonyl)-N-methyl-L-leucine, ethyl ester | 15327 | 18(10) 8(30) 19(100) |
| N-(9-Fluorenylmethoxycarbonyl)-N-methyl-L-leucine, benzyl ester | 15328 | 19(10) 29(30) 13(100) |
| N-(2-Methylfluorenyl-9-methoxycarbonyl)-L-leucine | 15477 | 41(10) 53(30) 69(100) |
| N-(2,3-Benzofluorenyl-9-methoxycarbonyl)-L-leucine | 15510 | 40(10) 40(30) 49(100) |
| N-(Fluorenyl-9-ethoxycarbonyl)-L-leucine | 15521 | 20(10) 15(30) 57(100) |
| N-[9H-(Fluoren-9-ylmethoxy)carbonyl]-L-leucine, tert-butyl ester | 15527 | 42(10) 34(30) 50(100) |
| N-[9H-(Fluorenyl-9-ylmethoxy)carbonyl]-L-leucine, amide | 15528 | 20(10) 27(30) 39(100) |
| N-[9H-(fluorenyl-9-ylmethoxy)carbonyl]-L-leucine, methylamide | 15529 | 50(10) 47(30) 50(100) |
| N-[9H-(Fluorenyl-9-ylmethoxy)carbonyl]-L-tert-leucine | 15573 | 23(10) 17(30) |
| N-[9H-(1-Methylfluorenyl-9-ylmethoxy)carbonyl]-L-leucine | 15638 | 37(10) 66(30) 82(100) |
| N-[9H-(Fluorenyl-9-ylmethoxy)carbonyl]-L-norleucine | 15667 | 22(10) 57(30) 80(100) |
| N-[H-(2,7-Dimethylfluorenyl-9-methoxy)carbonyl-L-leucine | 15669 | 12(10) 22(30) 60(100) |
| N-[(9H-(4,5-Dimethylfluorenyl-9-methoxy)carbonyl-L-leucine | 15670 | 78(10) 46(30) 50(100) |
| N-{9H-[3-(2-Methylfluorenyl-9]}-L-leucine-L-leucine | 15671 | 6(10) 10(30) 18(100) |
| N-[9H-(1-Methoxymethylfluorenyl-9-methoxy)carbonyl]-L-leucine | 15673 | 20(10) 26(30) 29(100) |
| N-[9H-(Fluorenyl-9-ylmethoxy)carbonyl]-L-neopentylglycine | 15676 | 26(10) 12(30) 44(100) |
| N-(9H-Fluorenyl-9-ylpropionyl)-L-tert-leucine | 15685 | 5(10) 23(30) 18(100) |
| N-[9H-(1-Methylfluorenyl-9-ylpropionyl)]-L-leucine | 15885 | 39(10) 49(30) 48(100) |
| N-[9H-(3-Fluoren-9-ylpropionyl)]-L-norleucine | 15894 | 0(10) 0(30) 34(100) |
| N-[9H-(3-Fluoren-9-ylpropionyl)]-L-homophenylanine | 15895 | 0(10) 0(30) 51(100) |
| N-[9H-(3-Fluoren-9-ylpropionyl)]-L-phenylanine | 15896 | 28(10) 24(30) 21(100) |

TABLE 9-continued

Inhibition of Ear Edema Caused by Xylene

| Compound | NPC Number | % Inhibition (dose, mg/kg) |
|---|---|---|
| N-[9H-(4-Methylfluoren-9-ylmethoxy)carbonyl]-L-tert-leucine | 15904 | 0(10) 10(30) 68(100) |
| N-[9H-(1-Methylfluoren-9-ylmethoxy)carbonyl]-L-norleucine | 15951 | 40(10) 62(30) 62(100) |
| N-[9H-(1-Methylfluoren-9-ylmethoxy)carbonyl]-L-norleucine | 15952 | 29(10) 39(30) 43(100) |
| N-[9H-(1-Methylfluoren-9-ylmethoxy)carbonyl]-L-homophenylalanine | 15961 | 41(10) 41(30) 57(100) |
| N-{9H-[3-(2-methoxylfuoren-9-yl)propionyl]}-L-leucine | 15968 | 23(10) 62(30) 57(100) |
| N-{9H-[3-(1-Methylfluoren-9-yl)propionyl]}-L-homophenylalanine | 15974 | 48(10) 57(30) 59(100) |
| N-{9H-{3-(4-Methylfluoren-9-yl)propionyl]}-L-leucine | 15975 | 51(10) 22(30) 49(100) |
| N-{9H-{3-(4-Methylfluoren-9-yl)propionyl]}-L-norleucine | 15976 | 59(10) 33(30) 62(100) |
| S-Benzyl-β,β-dimethyl-N-[9H-(fluoren-9-ylmethoxy)carbonyl]-D-cystein | 15953 | 46(10) 66(30) 60(100) |

EXAMPLE 47

Inhibition of Ear Edema Caused by Oxazolone (II)

CF-1 mice, 25-30 g body weight, five to six animals per group were used. The mice were sensitized to the irritant two weeks prior to the test by dribbling 100 μL of a 3% solution of oxazolone in acetone onto the abdominal skin of the animal. Test compounds were administered intraperitoneally as follows. The test compound was dissolved in dimethyl sulfoxide or 0.5% methylcellulose and 100 microliters (100 mg/kg) was injected 30 minutes prior to irritant. The irritant, 3% oxazolone in acetone, was added to the surface of the ear, 5 μL added to the upper surface and 5 μL added to the lower surface. After twenty four hours, the thickness of the ear was measured to 0.01 mm by a micrometer with loose drag, positioned at the lateral-most edge of the mid-point of the pinna. Data were calculated as the inhibition of increased ear thickness compared to control animals' receiving only the irritant. In general, % inhibition of greater than 20% is statistically significant (<0.05 or less, Student's t-test for unpaired data). The results are reported in Table 10.

TABLE 10

Inhibition of Ear Edema Caused by Oxazolone

| Compound | NPC Number | % Inhibition Intraperitoneal (dose, mg/kg) |
|---|---|---|
| Indomethacin (reference standard) | | 4(1) 35(3) |
| 4-Methylfluorenyl-9-methoxycarbonyl-L-leucine | 15325 | 22(10) 24(30) 49(100) |
| N-(9H-fluoren-9-ylpropionyl)-L-leucine | 15476 | 0(10) 5(30) 43(100) |
| N-(2-Methylfluorenyl-9-methoxycarbonyl)-L-leucine | 15477 | 3(10) 14(30) 43(100) |

TABLE 10-continued

Inhibition of Ear Edema Caused by Oxazolone

| Compound | NPC Number | % Inhibition Intraperitoneal (dose, mg/kg) |
|---|---|---|
| N-(2,3-Benzofluorenyl-9-methoxycarbonyl)-L-leucine | 15510 | −7(10)<br>3(30)<br>101(100) |
| N-(Fluorenyl-9-ethoxycarbonyl)-L-leucine | 15521 | 39(10)<br>45(30)<br>74(100) |
| N-[9H-(Fluoren-9-ylmethoxy)carbonyl]-L-leucine, tert-butyl ester | 15527 | 31(10)<br>33(30)<br>54(110) |
| N-[9H-(Fluorenyl-9-ylmethoxy)carbonyl]-L-leucine, amide | 15528 | 41(10)<br>25(30)<br>46(100) |
| N-[9H-(Fluorenyl-9-ylmethoxy)carbonyl]-L-leucine, methylamide | 15529 | 32(10)<br>41(30)<br>76(100) |
| N-[9H-(Fluorenyl-9-ylmethoxy)carbonyl]-L-tert-leucine | 15573 | 28(30)<br>48(100) |
| N-[9H-(1-Methylfluorenyl-9-ylmethoxy)carbonyl]-L-leucine | 15638 | 67(30)<br>74(100) |
| N-[9H-(Fluorenyl-9-ylmethoxy)carbonyl]-L-norleucine | 15667 | 13(10)<br>15(30)<br>71(100) |
| N-[9H-(2,7-Dimethylfluorenyl-9-methoxy)carbonyl-L-leucine | 15669 | −40(10)<br>84(30)<br>84(100) |
| N-[9H-(4,5-Dimethylfluorenyl-9-methoxy)carbonyl-L-leucine | 15670 | −36(10)<br>43(30)<br>540(100) |
| N-{9H-[3-(2-Methylfluorenyl-9]}-L-leucine-L-leucine | 15671 | 5(10)<br>20(30)<br>69(100) |
| N-{9H-[3-Fluorenyl-9)propionyl]}-L-leucine, sodium salt | 15672 | 11(10)<br>19(30)<br>35(100) |
| N-[9H-(1-Met methylsluorenyl-9-methoxy)carbonyl]-L-leucine | 15673 | (10)<br>12(30)<br>18(100) |
| N-[9H-(Fluorenyl-9-ylmethoxy)carbonyl]-L-neopentylglycine | 15676 | 0(10)<br>4(30)<br>50(100) |
| N-(9H-Fluorenyl-9-ylpropionyl)-L-tert-leucine | 15685 | 0(10)<br>30(30)<br>30(100) |
| N-[9H-(1-Methylfluorenyl-9-ylpropionyl)]-L-leucine | 15885 | 1(10)<br>8(30)<br>36(100) |
| N-[9H-(3-Fluoren-9-ylpropionyl)]-L-norleucine | 15894 | 29(10)<br>14(30)<br>35(100) |
| N-[9H-(3-Fluoren-9-ylpropionyl)]-L-homophenylalanine | 15895 | 4(10)<br>12(30)<br>71(100) |
| N-[9H-(4-Methylfluoren-9-ylmethoxy)carbonyl]-L-tert-leucine | 15904 | 21(10)<br>54(30)<br>79(100) |
| N-[9H-(1-Methylfluoren-9-ylmethoxy)carbonyl]-L-norleucine | 15951 | 33(10)<br>23(30)<br>49(100) |
| N-[9H-(1-Methylfluoren-9-ylmethoxy)carbonyl]-L-norleucine | 15952 | 21(10)<br>24(30)<br>72(100) |
| N-[9H-(1-Methylfluoren-9-ylmethoxy)carbonyl]-L-homophenylalanine | 15961 | 29(10)<br>23(30)<br>92(100) |
| N-{9H-[3-(2-Methoxyfluoren-9-yl)propionyl]}-L-leucine | 15968 | 24(10)<br>24(30)<br>66(100) |
| N-{9H-[3-(1-Methylfluoren-9-yl)propionyl]}-L-homophenylalanine | 15974 | 0(10)<br>23(30)<br>48(100) |
| N-{9H-{3-(4-Methylfluoren-9-yl)propionyl]}-L-leucine | 15975 | 36(10)<br>19(30)<br>73(100) |
| N-{9H-{3-(4-Methylfluoren-9-yl)propionyl]}-L-norleucine | 15976 | 10(10)<br>8(30)<br>73(100) |
| S-Benzyl-β,β-dimethyl-N-[9H-(fluoren-9-ylmethoxy)carbonyl]-D-cystein | 15953 | 0(10)<br>28(30)<br>79(100) |

EXAMPLE 48

Reverse Passive Artus Reaction (II)

Male CD rats weighing between 200 and 250 g were used. Test compounds were dissolved in dimethyl sulfoxide and 200 μL of this solution (100 mg/kg) were injected intraperitoneally one hour before administration of the antigen. The animals were anesthetized inhalationally with isoflurane and then injected through the penile vein with 1 mL of a solution of 2.5 mg of Evan's blue dye and 5.0 mg of human serum albumin in 1 mL of saline. This treatment was followed immediately by intracutaneous injections of 0.03 mL of anti-human albumin diluted to contain 3.65 mg of antibody at 3 sites along the midline back. Anesthesia was terminated and after three hours, the animals were sacrificed. The skin was removed and the blue stained areas cut out. The skin patches were soaked overnight in stoppered tubes containing 1 mL of 1 N potassium hydroxide at 37° C. Then 9 mL of a mixture of five parts of a 0.6 N phosphoric acid and thirteen parts of acetone were added to the tubes. The tube contents were agitated and centrifuged, and the absorbance measured at 620 nm. The data were calculated as inhibition of blueing by test compound compared to control animals receiving only antigen and antibody. The results are reported in Table 11.

TABLE 11

Reverse Passive Artus Reaction

| Compound | NPC Number | % Inhibition Intraperitoneal (dose, mg/kg) |
|---|---|---|
| Dexamethasone (reference standard) | | 4(10) |
| Indomethacin (reference standard) | | 5(1)<br>26(3)<br>27(10) |
| N-(9-Fluorenylmethoxycarbonyl)-N-methyl-L-leucine, methyl ester | 15326 | 19(100) |
| 2-[N-(9-Fluorenylmethoxycarbonyl)amino]-4-methylpentanol | 15427 | 14(100) |
| N-[(9H-fluoren-9-ylmethoxy)carbonyl]-L-leucine-1-glycine ester | 15430 | 48(100) |
| N-(9H-fluoren-9-ylpropionyl)-L-leucine | 15476 | 56(100) |
| N-(2-Methylfluorenyl-9-methoxycarbonyl)-L-leucine | 15477 | 53(100) |
| N-[9H-(2-Methoxylfluoren-9-ylmethoxycarbonyl]-L-leucine | 15489 | 64(100) |
| N-(2,3-Benzolfluorenyl-9-methoxycarbonyl)-L-leucine | 15510 | 50(100) |
| N-(Fluorenyl-9-ethoxycarbonyl)-L-leucine | 15521 | 63(100) |
| N-[9H-(Fluoren-9-ylmethoxy)carbonyl]-L-leucine, tert-butyl ester | 15527 | 4(100) |
| N-[9H-(Fluorenyl-9-ylmethoxy)carbonyl]-L-leucine, amide | 15528 | 0(100) |
| N-[9H-(Fluorenyl-9-ylmethoxy)carbonyl]-L-leucine, | 15529 | 0(100) |

TABLE 11-continued

Reverse Passive Artus Reaction

| Compound | NPC Number | % Inhibition Intraperitoneal (dose, mg/kg) |
|---|---|---|
| methylamide | | |
| N-[9H-(Fluorenyl-9-ylmethoxy)carbonyl]-L-tert-leucine | 15573 | 50(100) |
| N-[9H-(1-Methylfluorenyl-9-ylmethoxy)carbonyl]-L-leucine | 15638 | 68(100) |
| N-[9H-(Fluorenyl-9-ylmethoxy)carbonyl]-L-norleucine | 15667 | 63(100) |
| N-[9H-(2,7-Dimethylfluorenyl-9-methoxy)carbonyl-L-leucine | 15669 | 60(100) |
| N-[9H-(4,5-Dimethylfluorenyl-9-methoxy)carbonyl-L-leucine | 15670 | 82(100) |
| N-{9H-[3-(2-Methylfluorenyl-9]}-L-leucine-L-leucine | 15671 | 13(100) |
| N-{9H-[3-Fluorenyl-9)propionyl]}-L-leucine, sodium salt | 15672 | 34(100) |
| N-[9H-(1-Methoxymethylfluorenyl-9-methoxy)carbonyl]-L-leucine | 15673 | 46(100) |
| N-[9H-(Fluorenyl-9-ylmethoxy)carbonyl]-L-neopentylglycine | 15676 | 82(100) |
| N-(9H-Fluorenyl-9-ylpropionyl)-L-tert-leucine | 15685 | 42(100) |
| N-[9H-(1-Methylfluorenyl-9-ylpropionyl)]-L-leucine | 15885 | 49(100) |
| S-Benzyl-$\beta,\beta$-dimethyl-N-[9H-(fluoren-9-ylmethoxy)carbonyl]-D-cystein | 15953 | 68(100) |

EXAMPLE 49

Adjuvant Arthritis

Male Sprague Dawley rats, 150–200 g, were anesthetized with isoflurane. Drug was administered intraperitoneally in 0.5% methylcellulose or water. The rat was then injected in the distal third of the tail with 0.5 mL of saline or 0.5 mL of well-sonicated Freund's complete adjuvant containing 1 mg/mL *Mycobacterium tuberculosis*. Rats were then returned to their cages. On days 1 and 2 after the adjuvant injection, each rat was weighed and dosed with vehicle or drug suspension as before, but without anesthesia. On day 3, each rat was weighed and anesthetized. Blood was drawn by cardiac puncture into 0.2 mL of EDTA solution. Blood samples were microcentrifuged for 30 seconds. Then fibrinogen was converted into fibrin using sodium sulfite and the resulting fibrin was assayed using a Lowry protein assay to estimate initial fibrinogen levels. Percent inhibition by test compound was determined by subtracting fibrinogen level in non-Freund's adjuvant-injected rats from fibrinogen levels in rats injected with adjuvant alone and those rats injected with adjuvant plus test compound, and dividing the resultant fibrinogen increases in drug treated animals by non-drug treated animals and multiplying by 100.

TABLE 12

Inhibition of Adjuvant Induced Fibrinogen

Compound
NPC Number
% Inhibition
(dose, mg/kg)

N-[9H-(2,3-Benzofluoren-9-ylmethoxy)carbonyl]-L-leucine
(NPC 15510)
35(100)
N-[(9H-Fluoren-9-ylmethoxy)carbonyl]-L-leucine amide
(NPC 15528)

TABLE 12-continued

Inhibition of Adjuvant Induced Fibrinogen

Compound
NPC Number
% Inhibition
(dose, mg/kg)

0(100)

For purposes of Completing this disclosure, all references cited hereinabove are hereby incorporated by reference.

While the present invention has been described in some detail for purposes of clarity and understanding, one skilled in the art on reading this disclosure will appreciate that various changes in form and detail can be made without departing from the true scope of the invention.

What is claimed is:

1. A method of treating an inflammatory condition comprising administering to an animal in need of such treatment an amount of least one compound represented by the following formula:

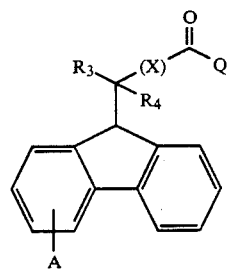

wherein:
X is methylene, ethylene, methyleneoxy, or oxygen;
Q is

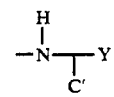

where C' is a residue of a lipophilic amino acid, and Y is —CO$_2$H, —CH$_2$OH, —CONR$_1$R$_2$, or —CO$_2$R$_1$ where R$_1$ and R$_2$ are hydrogen, alkyl, or aryl;

R$_3$ and R$_4$ are, independently, hydrogen, alkyl or aryl; and

A and B are, independently, hydrogen, fused phenyl, alkyl, aryl, alkaryl, aralkyl, alkoxy, alkoxyalkyl, halogen, or nitro;

or pharmaceutically acceptable salt thereof, sufficient to reduce or eliminate said inflammatory condition.

2. The method according to claim 1 wherein at least one of said alkyl, aryl, fused phenyl, alkaryl, aralkyl, alkoxy or alkoxyalkyl groups is substituted with a C$_{1-4}$alkyl.

3. The method according to claim 1 wherein said animal is a mammal.

4. The method according to claim 1 wherein R$_1$, R$_2$, R$_3$ and R$_4$ are, independently, hydrogen, (C$_{1-8}$)alkyl, or (C$_{6-12}$)aryl; and A and B are, independently, hydrogen, fused phenyl, (C$_{1-9}$)alkyl, (C$_{6-12}$)aryl, (C$_{1-9}$)alk(C$_{6-12}$)aryl, (C$_{6-12}$)ar(C$_{1-9}$)alkyl, (C$_{1-9}$)alkoxy, (C$_{1-9}$)alkoxy(C$_{1-9}$)alkyl, halogen, or nitro.

5. The method according to claim 4 wherein X is oxygen.

6. The method according to claim 5 wherein C' is a leucine residue and Y is —CO$_2$H.

7. The method according to claim 5 wherein C' is a phenylalanine residue and Y is —CO$_2$H.

8. The method according to claim 5 wherein A, B, R, and R are hydrogen.

9. The method according to claim 8 wherein C' is a L-leucine residue and Y is —CO$_2$H.

10. The method according to claim 8 wherein C' is a L-phenylalanine residue and Y is —CO$_2$H.

11. The method according to claim 8 wherein C' is a L-norleucine residue and Y is —CO$_2$H.

12. The method according to claim 8 wherein C' is a S-benzyl-$\beta,\beta$-dimethyl-D-cystein residue and Y is —CO$_2$H.

13. The method according to claim 8 wherein C' is a L-tert-leucine residue and Y is —CO$_2$H.

14. The method according to claim 8 wherein C' is a L-neopentylglycine residue and Y is —CO$_2$H.

15. The method according to claim 5 wherein $R_3$ and $R_4$ are hydrogen, A or B are at least one alkyl group, and Y is —CO$_2$H.

16. The method according to claim 15 wherein A is methyl group located in the 4 position of the fluorene ring, B is hydrogen, and C' is a leucine residue.

17. The method according to claim 15 wherein A is a methyl group located in the 4 position of the fluorene ring, B is hydrogen, and C' is a homophenylalanine residue.

18. The method according to claim 15 wherein A is a methyl group located in the 2 position of the fluorene ring, B is a methyl group located in the 7 position of the fluorene ring, and C' is a leucine residue.

19. The method according to claim 1 wherein X is methylene.

20. The method according to claim 19 wherein Y is —CO$_2$H.

21. The method according to claim 20 wherein A, B, $R_3$ and $R_4$ are hydrogen.

22. A compound of Formula 1:

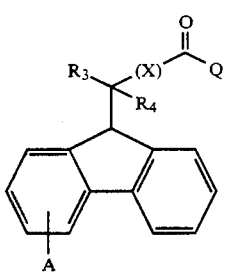

wherein:
X is methylene, ethylene, methyleneoxy, or oxygen;
Q is

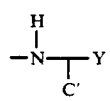

where C' is a residue of a lipophilic amino acid, and Y is —CO$_2$H, —CH$_2$OH, —CONR$_1$R$_2$, or —CO$_2$R$_1$ where R$_1$ and R$_2$ are hydrogen, alkyl, or aryl;

R$_3$ and R$_4$ are, independently, hydrogen, alkyl or aryl; and

A and B are, indecently, hydrogen, fused phenyl, alkyl, aryl, alkaryl, aralkyl, alkoxy, alkoxyalkyl, halogen, or nitro;
or pharmaceutically acceptable salt thereof,
with the proviso that when A, B, R$_3$ and R$_4$ are hydrogen and Y is —CO$_2$H (or salt thereof), X is not oxygen,
and with the further proviso that when A or B are, independently, hydrogen or halogen, R$_3$ and R$_4$ are hydrogen, X is oxygen, and Y is —CO$_2$H (or salt thereof), X is not oxygen,
and with the further proviso that when A or B are, independently, hydrogen or halogen, R$_3$ and R$_4$ are hydrogen, X is oxygen, and Y is —CO$_2$H (or salt thereof), C' is not an aromatic amino acid residue.

23. The compound according to claim 1 wherein at least one of said alkyl, aryl, fused phenyl, alkaryl, aralkyl, alkoxy or alkoxyalkyl groups is substituted with a C$_{1-4}$alkyl.

24. The compound according to claim 22 wherein R$_1$, R$_2$, R$_3$ and R$_4$ are independently, hydrogen (C$_{1-8}$)alkyl or (C$_{6-12}$)aryl; and A and B are, independently, hydrogen, fused phenyl, (C$_{1-9}$)alkyl, (C$_{6-12}$)aryl, (C$_{1-9}$)alk(C$_{6-12}$)aryl, (C$_{6-12}$)ar(C$_{1-9}$)alkyl, (C$_{1-9}$)alkoxy, (C$_{1-9}$)alkoxy(C$_{1-9}$)alkyl, halogen, or nitro.

25. The compound according to claim 24 wherein X is methylene.

26. The compound according to claim 25 wherein A, B, R, and R$_4$ are hydrogen.

27. The compound according to claim 26 wherein Y is —CO$_2$H.

28. The compound according to claim 24 wherein X is oxygen.

29. The compound according to claim 28 wherein R$_3$, and R$_4$ are hydrogen; and A or B is (C$_{1-9}$)alkyl.

30. The compound according to claim 29 wherein Y is —CO$_2$H.

31. The compound according to claim 30 wherein Q is leucine, isoleucine, norleucine or phenylalanine.

32. The compound according to claim 31 wherein A is a methyl group in the 4 position of the fluorene ring, B is hydrogen, and C' is a leucine residue.

33. The compound according to claim 30 wherein A is a methyl group in the 4 position of the fluorene ring, B is hydrogen, and C' is a homophenylalanine residue.

34. The compound according to claim 31 wherein A is a methyl group located in the 2 position of the fluorene ring, B is a methyl group located in the 7 position of the fluorene ring, and C' is a leucine residue.

35. The compound according to claim 24 wherein X is ethylene.

36. The compound according to claim 24 wherein X is methyleneoxy.

37. The compound according to claim 24 wherein Y is —CONR$_1$R$_2$.

38. The compound according to claim 37 wherein X is oxygen.

39. The compound according to claim 38 wherein R$_3$ and R$_4$ are hydrogen.

40. The compound according to claim 39 wherein R$_1$ is hydrogen and R$_2$ is hydrogen, alkyl or aryl.

41. The compound according to claim 40 wherein R$_2$ is alkyl.

42. The compound according to claim 41 wherein R$_2$ is methyl and Q is leucine.

43. The compound according to claim 24 wherein A, B, R₃ and R. are hydrogen, X is oxygen, Y is —CONHCH₃ and Q is leucine.

44. The compound according to claim 24 wherein A is a methyl group in the 2 position of the fluorene ring, B is a methyl group in the 7 position of the fluorene ring, R₃ and R₄ are hydrogen, X is oxygen, Y is —ONHCH₃ and Q is leucine.

45. The compound according to claim 24 wherein A is a methyl group in the 4 position of the fluorene ring, B, R₃ and R₄ are hydrogen, X is oxygen, Y is —CO₂H (or salt thereof) and Q is leucine.

46. The compound according to claim 24 wherein A is a methyl group in the 2 position of the fluorene ring, B is a methyl group in the 7 position of the fluorene ring, R₃ and R₄ are hydrogen, X is oxygen, Y is —CO₂H (or salt thereof) and Q is leucine.

47. The compound N-[9H-(fluoren-9-ylmethoxy)carbonyl]-L-tert-leucine.

48. The compound N-[9H-(fluoren-9-ylmethoxy)carbonyl]-L-neopentylglycine.

49. A pharmaceutical composition in dosage unit form suitable for use in producing an anti-inflammatory effect in an animal comprising, as an active ingredient, an amount of at least one compound of Formula:

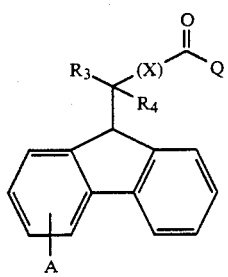

wherein:
X is methylene, ethylene, methyleneoxy, or oxygen;
Q is

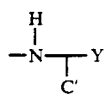

where C' is a residue of a lipophilic amino acid, and Y is —CO₂H, —CH₂OH, —CONR₁R₂, or —CO₂R₁ where R₁ and R₂ are hydrogen, alkyl, or aryl;

R₃ and R₄ are, independently, hydrogen, alkyl or aryl; and

A and B are, independently, hydrogen, fused phenyl, alkyl, aryl, alkaryl, aralkyl, alkoxy, alkoxyalkyl, halogen, or nitro;

or pharmaceutically acceptable salt thereof, sufficient to exert an anti-inflammatory effect, together with a pharmaceutically acceptable carrier or diluent.

50. The pharmaceutical composition according to claim 49 wherein said composition is in a form suitable for anal administration.

51. A pharmaceutical composition suitable for use in producing an anti-inflammatory effect in an animal comprising, as an active ingredient, an amount of at least one compound of Formula:

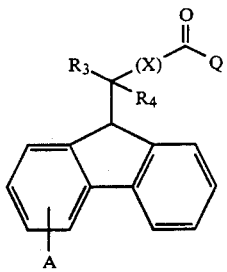

wherein:
X is methylene, ethylene, methyleneoxy, or oxygen;
Q is

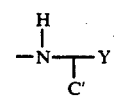

where C' is a residue of a lipophilic amino acid, and Y is —CO₂H, —CH₂OH, —CONR₁R₂, or —CO₂R₁ where R₁ and R₂ are hydrogen, alkyl, or aryl;

R₃ and R₄ are, independently, hydrogen, alkyl or aryl; and

A and B are, independently, hydrogen, fused phenyl, alkyl, aryl, alkaryl, aralkyl, alkoxy, alkoxyalkyl, halogen, or nitro;

or pharmaceutically acceptable salt thereof, sufficient to exert an anti-inflammatory effect, together with a pharmaceutically acceptable carrier or diluent, wherein said composition is in the form of a lotion, gel, ointment or cream.

52. A pharmaceutical composition suitable for use is producing an anti-inflammatory effect in an animal comprising, as an active ingredient, an amount of at least one compound of formula:

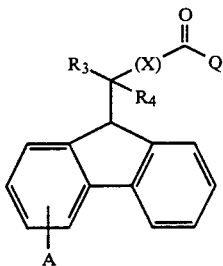

wherein:
X is methylene, ethylene, methyleneoxy, or oxygen;
Q is

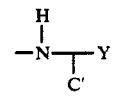

where C' is a residue of a lipophilic amino acid, and Y is —CO₂H, —CH₂OH, —CONR₁R₂, or —CO₂R₁ where R₁ and R₂ are hydrogen, alkyl, or aryl;

R₃ and R₄ are, independently, hydrogen, alkyl or aryl; and

A and B are, independently, hydrogen, fused phenyl, alkyl, aryl, alkaryl, aralkyl, alkoxy, alkoxyalkyl, halogen, or nitro;

or pharmaceutically acceptable salt thereof, sufficient to exert an anti-inflammatory effect, together with a pharmaceutically acceptable carrier or diluent, wherein said composition is in the form of a sterile aqueous solution.

53. A transdermal patch comprising a reservoir containing an amount of at least one compound represented by the following formula:

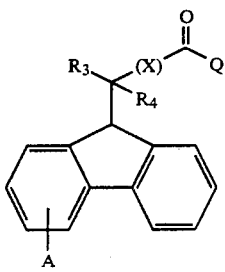

wherein:

X is methylene, ethylene, methyleneoxy, or oxygen;
Q is

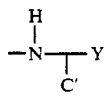

where C' is a residue of a lipophilic amino acid, and Y is —CO$_2$H, —CH$_2$OH, —CONR$_1$R$_2$, or —CO$_2$R$_1$ where R$_1$ and R$_2$ are hydrogen, alkyl, or aryl;

R$_3$ and R$_4$ are, independently, hydrogen, alkyl or aryl; and

A and B are, independently, hydrogen, fused phenyl, alkyl, aryl, alkaryl, aralkyl, alkoxy, alkoxyalkyl, halogen, or nitro;

or pharmaceutically acceptable salt thereof, sufficient to exert an anti-inflammatory effect, wherein said patch is constructed such that said compound of Formula 1 is available for transdermal administration to animal wearing said patch.

54. A pharmaceutical composition in dosage unit form suitable for use in producing an anti-inflammatory effect in an animal comprising, as an active ingredient, an amount of at least one compound of formula:

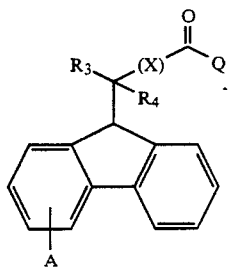

wherein:

X is methylene, ethylene, methyleneoxy, or oxygen;
Q is

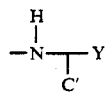

where C' is a residue of a lipophilic amino acid, and Y is —CO$_2$H, —CH$_2$OH, —CONR$_1$R$_2$, or —CO$_2$R$_1$ where R$_1$ and R$_2$ are hydrogen, alkyl, or aryl;

R$_3$ and R$_4$ are, independently, hydrogen, alkyl or aryl; and

A and B are, independently, hydrogen, fused phenyl, alkyl, aryl, alkaryl, aralkyl, alkoxy, alkoxyalkyl, halogen, or nitro;

or pharmaceutically acceptable salt thereof, sufficient to exert an anti-inflammatory effect, with the proviso that when A, B, R$_3$ and R$_4$ are hydrogen and Y is —CO$_2$H, (or salt thereof), X is not oxygen, and with the further proviso that when A or B are, independently, hydrogen or halogen, R$_3$ and R$_4$ are hydrogen, X is oxygen, and Y is —CO$_2$H, (or salt thereof), C' is not an aromatic amino acid residue, together with a pharmaceutically acceptable carrier or diluent.

55. A pharmaceutical composition suitable for use in producing an anti-inflammatory effect in an animal comprising, as an active ingredient, an amount of at lest one compound of Formula:

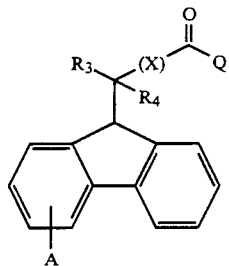

wherein:

X is methylene, ethylene, methyleneoxy, or oxygen;
Q is

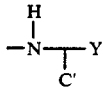

where C' is a residue of a lipophilic amino acid, and Y is —CO$_2$H, —CH$_2$OH, —CONR$_1$R$_2$, or —CO$_2$R$_1$ where R$_1$ and R$_2$ are hydrogen, alkyl, or aryl;

R$_3$ and R$_4$ are, independently, hydrogen, alkyl or aryl; and

A and B are, independently, hydrogen, fused phenyl, alkyl, aryl, alkaryl, aralkyl, alkoxy, alkoxyalkyl, halogen, or nitro;

or pharmaceutically acceptable salt thereof, sufficient to exert an anti-inflammatory effect, with the proviso that when A, B, R$_3$ and R$_4$ are hydrogen and Y is —CO$_2$H, (or salt thereof), X is not oxygen, and with the further proviso that when A or B are, independently, hydrogen or halogen, R$_3$ and R$_4$ are hydrogen, X is oxygen, and Y is —CO$_2$H, (or salt thereof), C' is not an aromatic amino acid residue, together with a pharmaceutically acceptable acceptable carrier or diluent, wherein said composition is in the form of a lotion, gel, ointment or cream.

56. A pharmaceutical composition suitable for use in producing an anti-inflammatory effect in an animal comprising, as an active ingredient, and amount of at least one compound of Formula:

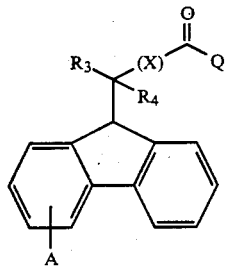

wherein:
X is methylene, ethylene, methyleneoxy, or oxygen;
Q is

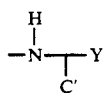

where C' is a residue of a lipophilic amino acid, and Y is —CO$_2$H, —CH$_2$OH, —CONR$_1$R$_2$, or —CO$_2$R$_1$ where R$_1$ and R$_2$ are hydrogen, alkyl, or aryl;

R$_3$ and R$_4$ are, independently, hydrogen, alkyl or aryl; and

A and B are, independently, hydrogen, fused phenyl, alkyl, aryl, alkaryl, aralkyl, alkoxy, alkoxyalkyl, halogen, or nitro;

or pharmaceutically acceptable salt thereof, sufficient to exert an anti-inflammatory effect, with the proviso that when A, B, R$_3$ and R$_4$ are hydrogen and Y is —CO$_2$H, (or salt thereof), X is not oxygen, and with the further proviso that when A or B are, independently, hydrogen or halogen, R$_3$ and R$_4$ are hydrogen, X is oxygen, and Y is —CO$_2$H, (or salt thereof), C' is not an aromatic amino acid residue, together with a pharmaceutically acceptable acceptable carrier or diluent, wherein said composition is in the form of a sterile aqueous solution.

57. A transdermal patch comprising a reservoir containing an amount of at least one compound represented by the following formula:

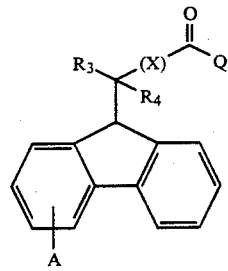

wherein:
Q is

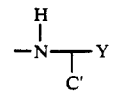

where C' is a residue of a lipophilic amino acid, and Y is —CO$_2$H, —CH$_2$OH, —CONR$_1$R$_2$, or —CO$_2$R$_1$ where R$_1$ and R$_2$ are hydrogen, alkyl, or aryl;

R$_3$ and R$_4$ are, independently, hydrogen, alkyl or aryl; and

A and B are, independently, hydrogen, fused phenyl, alkyl, aryl, alkaryl, aralkyl, alkoxy, alkoxyalkyl, halogen, or nitro;

or pharmaceutically acceptable salt thereof, sufficient to exert an anti-inflammatory effect, with the proviso that when A, B, R$_3$ and R$_4$ are hydrogen and Y is —CO$_2$H, (or salt thereof, X is not oxygen, and with the further proviso that when A or B are, independently, hydrogen or halogen, R$_3$ and R$_4$ are hydrogen, X is oxygen, and Y is —CO$_2$H, (or salt thereof), C' is not an aromatic amino acid residue, wherein said patch is constructed such that said compound of Formula 1 is available for transdermal administration to animal wearing said patch.

* * * * *

UNITED STATES PATENT AND TRADEMARK OFFICE
CERTIFICATE OF CORRECTION

PATENT NO. : 5,079,260

DATED : Jan. 7, 1992

INVENTOR(S) : Moshe Weitzberg, Ronald Burch, Barry Shearer

It is certified that error appears in the above-identified patent and that said Letters Patent is hereby corrected as shown below:

In Claims 1 (Col.42, ln.34), 22 (Col.43, ln.54) 49 (Col.45, ln 38), 51 (Col. 46, ln. 12), 52 (Col. 46, ln. 53), 53 (Col. 47, ln. 23), 54 (Col. 47, ln. 63), 55 (Col. 48, ln. 43), 56 (Col. 49, ln. 22), and 57 (Col. 50, ln. 18), to the unsubstituted 6-membered aromatic ring of Formula I, should be added a --B-- substituent as shown in Formula I at Col. 3, lns. 1-12.

In Claim 8 at Col. 43, lns.7-8, "R, and R" should be replaced by --$R_3$ and $R_4$--.

In Claim 22 at Col. 44, ln.3, "indecently" should be replaced by --independently--.

Col. 44, line 31, claim 26, "indecently" should read --$R_3$--.

In Claim 57 at Col. 50, ln. 20, --X is methylene, ethylene, methyleneoxy, or oxygen; -- should be added.

Signed and Sealed this

Twentieth Day of April, 1993

Attest:

MICHAEL K. KIRK

Attesting Officer

Acting Commissioner of Patents and Trademarks